US005707803A

United States Patent [19]
Lamb et al.

[11] Patent Number: 5,707,803
[45] Date of Patent: Jan. 13, 1998

[54] DNA REGULATORY ELEMENTS RESPONSIVE TO CYTOKINES AND METHODS FOR THEIR USE

[75] Inventors: Ian Peter Lamb; H. Martin Seidel, both of San Diego, Calif.

[73] Assignee: Ligand Pharmaceuticals, Inc., San Diego, Calif.

[21] Appl. No.: 410,780

[22] Filed: Mar. 27, 1995

Related U.S. Application Data

[63] Continuation-in-part of Ser. No. 228,934, Apr. 14, 1994, abandoned.
[51] Int. Cl.$^6$ .............................. C12Q 1/68; C07H 21/04; C12N 15/11; C12N 15/67
[52] U.S. Cl. ..................... 435/6; 435/69.1; 435/172.3; 435/320.1; 536/24.1; 935/8; 935/39; 935/41
[58] Field of Search ..................... 536/24.1; 435/69.1, 435/172.3, 6, 4, 320.1; 935/8, 39, 41

[56] References Cited

PUBLICATIONS

Altemeyer et al., "Multiple cytokine interactions regulate Ly–6E antigen expression: Cooperative Ly–6E induction by IFNs, TNF, and IL–1 in a T–cell lymphoma and its induction–deficient variants", Cell. Immun. 138:94–107, 1991.
Bothwell et al., "Isolation and expression of an IFN–responsive Ly–6C chromosomal gene", J. Immunol. 140: 2815–2820, 1988.
Chalfie et al. Science 263: 802–805, Feb. 11, 1994.
King et al. Dictionary of Genetics, 2nd Ed., Oxford University Press, New York, p. 272, 1985.
Molecular Biology Reagents/Protocols, United States Biochemical Corp., Cleveland, Ohio, p. 618, 1991.
Amaya et al., J. Biochem. 103: 177–181, 1988.
Heilig et al., Nucleic Acids Res. 10: 4363–4382, 1982.
Anderson et al., J. Mol. Biol. 156:683–717, 1982.
Yang et al., Gene 91: 247–253, 1990.
Wilde et al., Nature 297: 83–84, 1982.
Clary et al., Nucleic Acids Res. 11: 6859–6872, 1983.
Haas et al., Gene 113: 129–133, 1992.
Masuda et al., Nucleic Acids Res. 18: 3055, 1990.
Wallace et al., Methods Enzymol. 152: 432–443, 1987.
Lew, D.; Decker, T.; Strehlow, I.; and Darnell, J., "Overlapping Elements in the Guanylate–Binding Protein Gene Promoter Mediate Transcriptional Induction by Alpha and Gamma Interferons," *Molecular and Cellular Biology*, vol. 11, No. 01, pp. 182–191 (1991).
Decker, T.; Lew, D.; and Darnell, J., "Two Distinct Alpha–Interferon–Dependent Signal Transduction Pathways May Contribute to Activation of Transcription of the Guanylate–Binding Protein Gene," *Molecular and Cellular Biology*, vol. II, No. 10, pp. 5147–5153 (1991).
Decker, T.; Lew, D.; Mirkovitch, J.; and Darnell, J., "Cytoplasmic activation of GAF, an IFN–γ–regulated DNA–binding factor," *The EMBO Journal*, vol. 10, No. 4, pp. 927–932 (1991).

Akira, S.; Nishio, Y.; Inoue, M.; Wang, X.; Wei, S.; Matsusaka, T.; Yoshida, K.; Sudo, T.; Naruto, M.; and Kishimoto, T., "Molecular Cloning of APRF, a Novel IFN–Stimulated Gene Factor 3 p91–Related Transcription Factor Involved in the gp 130–Mediated Signaling Pathway," *Cell*, vol. 77, pp. 63–71 (1994).
Hattori, M.; Abraham, L.; Northemann, W.; and Fey, G., "Acute–phase reaction induces a specific complex between hepatic nuclear proteins and the interleukin 6 response element of the rat $\alpha_2$–macroglobulin gene," *Proc. Natl. Acad. Sci. USA*, vol. 87, pp. 2364–2368 (1990).
Wegenka, U.; Buschmann, J.; Lütticken, C.; Heinrich, P.; and Horn, F., "Acute–Phase Response Factor, a Nuclear Factor Binding to Acute–Phase Response Elements, is Rapidly Activated by Interleukin–6 at the Posttranslational Level," *Molecular and Cellular Biology*, vol. 13, No. 1, pp. 276–288 (1993).
Ito, T.; Tanahashi, H.; Misumi, Y.; and Sakaki, Y., "Nuclear factors interacting with an interleukin–6 responsive element of a rat $\alpha_2$–macroglobulin gene," *Nucleic Acids Research*, vol. 17, No. 22, pp. 9425–9435 (1989).
Hocke, G.; Barry, D.; and Fey, G., "Synergistic Action of Interleukin–6 and Glucocorticoids Is Mediated by the Interleukin–6 Response Element of the Rat $\alpha_2$–Macroglobulin Gene," *Molecular and Cellular Biology*, vol. 12, No. 5, pp. 2282–2294 (1992).
Yuan, J.; Wegenka, U.; Lütticken, C.; Buschmann, J.; Decker, T.; Schindler, C.; Heinrich, P.; and Horn, F., "The Signalling Pathways of Interleukin–6 and Gamma Interferon Converge by the Activation of Different Transcription Factors Which Bind to Common Responsive DNA Elements," *Molecular and Cellular Biology*, vol. 14, No. 3, pp. 1657–1668 (1994).
Kunz, D.; Zimmermann, R.; Heisig, M.; and Heinrich, P., "Identification of the promoter sequences involved in the interleukin–6 dependent expressioin of the rat $\alpha_2$–macroglobulin gene," *Nucleic Acids Research*, vol. 17, No. 3, pp. 1121–1138 (1989).

(List continued on next page.)

*Primary Examiner*—Jasemine C. Chambers
*Assistant Examiner*—Scott D. Priebe
*Attorney, Agent, or Firm*—J. Scott Elmer

[57] ABSTRACT

The present invention provides oligonucleotide sequences comprising DNA regulatory elements comprising point mutations of Ly6E GAS element that bind activated transcriptional regulatory proteins in response to signaling molecules, such as cytokines. Further, the present invention also provides DNA constructs comprising the oligonucleotide sequences, cells transfected with the DNA constructs, and methods of using the DNA constructs and transfected cells to provide for the controlled expression of structural genes, for the detection and recovery of transcriptional regulatory proteins, and for measuring the ability of compounds to act as agonist and antagonists of gene transcription.

27 Claims, 6 Drawing Sheets

PUBLICATIONS

Khan, K.; Lindwall, G.; Maher, S.; and Bothwell, A., "Characterization of Promoter Elements of an Interferon–Inducible Ly–6E/A Differentiation Antigen, Which Is Expressed on Activated T Cells and Hematopoietic Stem Cells," *Molecular and Cellular Biology*, vol. 10, No. 10, pp. 5150–5159 (1990).

Khan, K.; Shuai, K.; Lindwall, G.; Maher, S.; Darnell, J.; and Bothwell, A., "Induction of the Ly–6A/E gene by interferon α/β and γ requires a DNA element to which a tyrosine–phosphorylated 91–kDa protein binds," *Proc. Natl. Acad. Sci. USA*, vol. 90, pp. 6806–6810 (1993).

Sadowski, H. and Gilman, M., "Cell–free activation of a DNA–binding protein by epidermal growth factor," *Nature*, vol. 362, pp. 79–83 (1993).

Wagner, B.; Hayes, T.; Hoban, C.; and Cochran, B., "The SIF binding element confers sis/PDGF inducibility onto the c–fos promoter," *The EMBO Journal*, vol. 9., No. 13, pp. 4477–4484 (1990).

Strehlow, I. and Decker, T., "Transcriptional inductiion of IFN–γ–responsive genes is modulated by DNA surrounding the interferon stimulation response element," *Nucleic Acids Research*, vol. 20, No. 15, pp. 3865–3872 (1992).

Wong, P.; Severns, C.; Guyer, N.; and Wright, T., "A Unique Palindromic Element Meidates Gamma Interferon Induction of mig Gene Expression," *Molecular and Cellular Biology*, vol. 14, No. 2, pp. 914–922 (1994).

Silvennoinen, O.; Schindler, C.; Schlessinger, J.; and Levy, D., "Ras–Independent Growth Factor Signaling by Transcription Factor Tyrosine Phosphorylation," *Science*, vol. 261, pp. 1736–1739 (1993).

Ruff–Jamison, S.; Chen, K.; and Cohen, S., "Induction by EGF and Interferon–γ of Tyrosine Phosphorylated DNA Binding Proteins in Mouse Liver Nuclei," *Science*, vol. 261, pp. 1733–1736 (1993).

Larner, A.; David, M.; Feldman, G.; Igarashi, K.; Hackett, R., Webb, D.; Sweitzer, S.; Petricoin, E.; and Finbloom, D., "Tyrosine Phosphorylation of DNA Binding Proteins by Multiple Cytokines," *Science*, vol. 261, pp. 1730–1733 (1993).

Shuai, K.; Stark, G.; Kerr, I.; and Darnell, J., "A Single Phosphotyrosine Residue of Stat91 Required for Gene Activation by Interferon–γ," *Science*, vol. 261, pp. 1744–1746 (1993).

Sadowski, H.; Shuai, K.; Darnell, J.; and Gilman, M., "A Common Nuclear Signal Transduction Pathway Activated by Growth Factor and Cytokine Receptors," *Science*, vol. 261, pp. 1739–1744 (1993).

Kanno, Yuka; Kozak, C.; Schindler, C.; Driggers, P.; Ennist, D.; Gleason, S.; Darnell, J.; and Ozato, K., "The Genomic Structure of the Murine ICSBP Gene Reveals the Presence of the Gamma Interferon–Responsive Element, to Which an ISGF3α Subunit (or Similar) Molecule Binds," *Molecular and Cellular Biology*, vol. 13, No. 7, pp. 3951–3963 (1993).

Harroch, S.; Revel, M.; and Chebath, J., "Induction by interleukin–6 of interferon regulatory factor 1 (IRF–1) gene expression through the palindromic interferon response element pIRE and cell type–dependent control of IRF–1 binding to DNA," *The EMBO Journal*, vol. 13, No. 8, pp. 1942–1949 (1994).

Sims, S.; Cha, Y.; Romine, M.; Gao, P.; Gottlieb, K.; and Deisseroth, A., "A Novel Interferon–Inducible Domain: Structural and Functional Analysis of the Human Interferon Regulatory Factor 1 Gene Promoter," *Molecular and Cellular Biology*, vol. 13, No. 1, pp. 690–702 (1993).

Pearse, R.; Feinman, R.; Shuai, K.; Darnell, J.; and Ravetch, J., "Interferon γ–induced transcription of the high–affinity Fc receptor for IgG requires assembly of a complex that includes the 91–kDa subunit of transcription factor ISGF3," *Proc. Natl. Acad. Sci. USA*, vol. 90, pp. 4314–4318 (1993).

Pearse, R.; Feinman, R.; and Ravetch, J., "Characterization of the promoter of the human gene encoding the high affinity IgG receptor: Transcriptional induction by γ–interferon is mediated through common DNA response elements," *Proc. Natl. Acad. Sci. USA*, vol. 88, pp. 11305–11309 (1991).

Kotanides, H. and Reich, N., "Requirement of Tyrosine Phosphorylation for Rapid Activation of a DNA Binding Factor by IL–4," *Science*, vol. 262, pp. 1265–1267 (1993).

Schindler, C.; K. Kashleva, H.; Pernis, A.; Pine, R.; and Rothman, P., "STF–IL–4; a novel IL–4–induced signal transducing factor," *The EMBO Journal*, vol. 13, No. 6, pp. 1350–1356 (1994).

Li, P.; He, X.; Gerrero, M.; Mok, M.; Aggarwal, A.; and Rosenfeld, M., "Spacing and orientation of bipartite DNA–binding motifs as potential functional determinants for POU domain factors" *Genes & Development*, vol. 7, pp. 2483–2496 (1993).

Carlberg, C., "RXR–Independent Action of the Receptors for Thyroid Hormone, Retinoid Acid and Vitamin D on Inverted Palindromes," *Biochemical and Biophysical Research Communications*, vol. 195, No. 3, pp. 1345–1353 (1993).

Mangelsdorf, D., et al., "Retinoid Receptors," *The Retinoids: Biology, Chemistry and Medicine*, 2nd ed., pp. 331–332 (1994).

Umesono, K.; Murakami, K.; Thompson, C.; and Evans, R., "Direct Repeats as Selective Response Elements for the Thyroid Hormone, Retinoic Acid, and Vitamin $D_3$ Receptors," Cell. vol. 65, pp. 1255–1266 (1991).

Näär, A.; Boutin, J.; Lipkin, S.; Yu, V.; Holloway, J.; Glass, C.; and Rosenfeld, M., "The Orientation and Spacing of Core DNA–Binding Motifs Dictate Selective Transcriptional Responses to Three Nuclear Receptors," *Cell*, vol. 65, pp. 1267–1279 (1991).

Reid, L.; Brasnett, A.; Gilbert, C.; Porter, A.; Gewert, D.; Stark, G.; and Kerr, I.,"A single DNA response element can confer inducibility by both α– and γ–interferons," *Proc. Natl. Acad. Sci. USA*, vol. 86, pp. 840–844 (1989).

Wakao, H., Gouilleux, F., and Groner, B., "Mammary gland factor (MGF) is a novel member of the cytokine regulated transcription factor gene family and confers the prolactin response," *The EMBO Journal*, vol. 13, No. 9, pp. 2182–2191 (1994).

Mui, A., Wakao, H., O'Farrell, A., Harada, N., and Miyajima, A., "Interleukin–3, granulocyte–macrophage colony stimulating factor and interleukin–5 transduce signals through two STAT5 homologs," *The EMBO Journal*, vol. 14, No. 6, pp. 1166–1174 (1995).

Drachman, J., Griffin, J., and Kaushansky, K., "The c–Mpl Ligand (Thrombopoietin) Stimulates Tyrosine Phosphorylation of Jak2, Shc, and c–Mpl," *The Journal of Biological Chemistry*, vol. 270, No. 10, pp. 4979–4982 (1995).

Beading, C., Guschin, D., Witthuhn, B., Ziemiecki, A., Ihle, J., Kerr, I., and Cantrell, D., "Activation of JAK kinases and STAT proteins by interleukin-2 and interferon α, but not the T cell antigen receptor, in human T lymphocytes," *The EMBO Journal*, vol. 13, No. 23, pp. 5605–5615 (1994).

Gouilleux, F., Wakao, H., Mundt, M., and Groner, B., "Prolactin induces phosphorylation of Tyr694 of Stat5 (MGF), a prerequisite for DNA binding and induction of transcription," *The EMBO Journal*, vol. 13, No. 18, pp. 4361–4369 (1994).

Standke, G., Meier, V., and Groner, B., "Mammary Gladn Factor Activated by Prolactin in Mammary Epithelial Cells and Acute-Phase Response Factor Activated by Interleukin-6 in Liver Cells Share DNA Binding and Transactivation Potential," *Molecular Endocrinology*, vol. 8, No. 4, pp. 469–477 (1994).

Delphin, S., and Stavnezer, J., "Characterization of an Interleukin 4(IL-4) Responsive Region in the Immunoglobulin Heavy Chain Germline & Promoter: Regulation by NF-IL-4, a C/EBP Family Member and NF-kB/p50," *J. Exp. Med.*, vol. 181, pp. 181–192 (1995).

Albrecht, ., Peiritsch, S., and Woisetschläger, M., "A bifunctional control element in the human IgE germline promoter involved in repression and IL-4 activation," *International Immunology*, vol. 6, No. 8, pp. 1143–1151 (1994).

Coffer, P., Lutticken, C., Puijenbroek, A., Jonge, M., Horn, F., and Kruijer, W., "Transcriptional regulation of the junB promoter: analysis of STAT-mediated signal transduction," *Oncogene*, vol. 10(5) pp. 985–994 (1995).

Fujitani, Y., Nakajima, K., Kojima, H., Nakae, K., Takeda, ., and Hirano, T., "Transcriptional Activation of the IL-6 Response Element in the JunB Promoter is Mediated by Multiple STAT Family Proteins," *Biochemical and Biophysical Research Communications*, vol. 202, No. 2, pp. 1181–1187 (1994).

Hou, J., Schindler, U., Henzel, W., Ho, T., Brasseur, M., and McKnight, S., "An Interleukin-4–Induced Transcription Factor: IL-4 STAT," *Science*, vol. 265, pp. 1701–1706 (1994).

Rothman, P.; Kreider, B.; Azam, M.; Levy, D.; Wegenka, U.; Eilers, A.; Decker, T.; Horn, F.; Hashleva, H.; Ihle, J.; and Schindler, C., "Cytokines and Growth Factors Signal Through Tyrosine Phosphorylation of a Family of Related Transcription Factors," *Immunity*, vol. 1 pp. 457–468 (1994).

Lamb, P.; Kessler, L. V.; Suto, C.; Levy, D.E.; Seidel, H.M.; Stein, R.B.; and Rosen, J., "Rapid Activation of Proteins that Interact with the Interferon-γ Activation Site in Response to Multiple Cytokines" *Blood*, vol. 83, No. 8, pp. 2063–2071 (1994).

FIG. 1

| Sequence | IFN-γ | IL-6 | GM-CSF | IL-4 |
|---|---|---|---|---|
| WT TATTCCTGTAAGT | 4 | 4 | 2 | 2 |
| 2G | 0 | 1 | 0 | 0 |
| 2C | 4 | 3 | 1 | 3 |
| 2T | 0 | 0 | 0 | 0 |
| 3A | 1 | 1 | 0 | 0 |
| 3G | 1 | 0 | 0 | 0 |
| 3C | 1 | 0 | 0 | 0 |
| 4A | 3 | 1 | 0 | 0 |
| 4G | 3 | 1 | 0 | 0 |
| 4C | 0 | 0 | 0 | 0 |
| 5A | 1 | 2 | 0 | 0 |
| 5T | 1 | 1 | 0 | 1 |
| 5G | 0 | 0 | 0 | 0 |
| 6A | 1 | 0 | 0 | 1 |
| 6T | 3 | 2 | 3 | 3 |
| 6G | 1 | 0 | 1 | 1 |
| 7A | 0 | 0 | 0 | 0 |
| 7G | 4 | 5 | 1 | 3 |
| 7C | 5 | 5 | 1 | 1 |
| 8A | 4 | 2 | 1 | 1 |
| 8T | 3 | 0 | 1 | 1 |
| 8C | 3 | 1 | 0 | 1 |
| 9A | 0 | 1 | 0 | 0 |
| 9G | 5 | 5 | 4 | 4 |
| 9C | 3 | 1 | 1 | 1 |
| 10G | 1 | 0 | 1 | 1 |
| 10T | 3 | 3 | 2 | 2 |
| 10C | 3 | 3 | 0 | 0 |
| 11G | 2 | 1 | 0 | 1 |
| 11T | 0 | 0 | 0 | 0 |
| 11C | 3 | 1 | 0 | 1 |

FIG. 5

| GAS Element | STAT1α Binding | Fold Induction (IFN-γ) |
|---|---|---|
| Ly6E | 4 | 66x |
| 7C | 5 | 29.5x |
| 8A | 4 | 38.4x |
| 4G | 3 | 1x |
| 8T | 3 | 1x |

IP: αS1

IP: αS3

SEQUENCE LISTING ( 1 ) GENERAL INFORMATION:

( i i i ) NUMBER OF SEQUENCES: 77

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:1:

TATTCCTGGA AGT                                                       13

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:2:

TATTCCGGTA AGT                                                       13

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

(x i) SEQUENCE DESCRIPTION: SEQ ID NO:3:

TCTTCCTGTA AGT                                                                                13

(2) INFORMATION FOR SEQ ID NO:4:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:4:

TATTCTTGTA AGT                                                                                13

(2) INFORMATION FOR SEQ ID NO:5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:5:

TATTCCTGTT AGT                                                                                13

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:6:

TATTCCCGTA AGT                                                                                13

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:7:

TATTCCTATA AGT                                                                                13

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear ( i i ) MOLECULE TYPE: other nucleic acid
   ( A ) DESCRIPTION: /desc = "OTHER NUCLEIC ACID,
       SYNTHETIC DNA"

( x i ) SEQUENCE DESCRIPTION: SEQ ID NO:8:

TATTCCTGTC AGT  13

( 2 ) INFORMATION FOR SEQ ID NO:9:

( i ) SEQUENCE CHARACTERISTICS:
   ( A ) LENGTH: 13 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "OTHER NUCLEIC ACID,
       SYNTHETIC DNA"

( x i ) SEQUENCE DESCRIPTION: SEQ ID NO:9:

TATACCTGTA AGT  13

( 2 ) INFORMATION FOR SEQ ID NO:10:

( i ) SEQUENCE CHARACTERISTICS:
   ( A ) LENGTH: 13 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "OTHER NUCLEIC ACID,
       SYNTHETIC DNA"

( x i ) SEQUENCE DESCRIPTION: SEQ ID NO:10:

TATGCCTGTA AGT  13

( 2 ) INFORMATION FOR SEQ ID NO:11:

( i ) SEQUENCE CHARACTERISTICS:
   ( A ) LENGTH: 13 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "OTHER NUCLEIC ACID,
       SYNTHETIC DNA"

( x i ) SEQUENCE DESCRIPTION: SEQ ID NO:11:

TATTCCTTTA AGT  13

( 2 ) INFORMATION FOR SEQ ID NO:12:

( i ) SEQUENCE CHARACTERISTICS:
   ( A ) LENGTH: 13 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "OTHER NUCLEIC ACID,
       SYNTHETIC DNA"

( x i ) SEQUENCE DESCRIPTION: SEQ ID NO:12:

TATTCCTCTA AGT  13

( 2 ) INFORMATION FOR SEQ ID NO:13:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
        SYNTHETIC DNA"

( x i ) SEQUENCE DESCRIPTION: SEQ ID NO:13:

TATTCCTGCA AGT 13

( 2 ) INFORMATION FOR SEQ ID NO:14:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
        SYNTHETIC DNA"

( x i ) SEQUENCE DESCRIPTION: SEQ ID NO:14:

TATTCCTGTA CGT 13

( 2 ) INFORMATION FOR SEQ ID NO:15:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
        SYNTHETIC DNA"

( x i ) SEQUENCE DESCRIPTION: SEQ ID NO:15:

TTTTCCTGTA AGTG 14

( 2 ) INFORMATION FOR SEQ ID NO:16:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
        SYNTHETIC DNA"

( x i ) SEQUENCE DESCRIPTION: SEQ ID NO:16:

CACTTACAGG AAAA 14

( 2 ) INFORMATION FOR SEQ ID NO:17:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
        SYNTHETIC DNA"

( x i ) SEQUENCE DESCRIPTION: SEQ ID NO:17:

TGTTCCTGTA AGTG 14

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:18:

CACTTACAGG AACA 14

(2) INFORMATION FOR SEQ ID NO:19:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:19:

TCTTCCTGTA AGTG 14

(2) INFORMATION FOR SEQ ID NO:20:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:20:

CACTTACAGG AAGA 14

(2) INFORMATION FOR SEQ ID NO:21:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:21:

TAATCCTGTA AGTG 14

(2) INFORMATION FOR SEQ ID NO:22:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid ( A ) DESCRIPTION: /desc = "OTHER NUCLEIC ACID, SYNTHETIC DNA"

( x i ) SEQUENCE DESCRIPTION: SEQ ID NO:22:

CACTTACAGG ATTA  14

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:23:

GATCATAGTC CTGTAAGTG  19

( 2 ) INFORMATION FOR SEQ ID NO:24:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:24:

GATCCACTTA CAGGACTAT  19

( 2 ) INFORMATION FOR SEQ ID NO:25:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:25:

GATCATACTC CTGTAAGTG  19

( 2 ) INFORMATION FOR SEQ ID NO:26:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:26:

GATCCACTTA CAGGAGTAT  19

( 2 ) INFORMATION FOR SEQ ID NO:27:

( i ) SEQUENCE CHARACTERISTICS:
        ( A ) LENGTH: 14 base pairs (B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:27:

TATACCTGTA AGTG 14

(2) INFORMATION FOR SEQ ID NO:28:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:28:

CACTTACAGG TATA 14

(2) INFORMATION FOR SEQ ID NO:29:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:29:

TATGCCTGTA AGTG 14

(2) INFORMATION FOR SEQ ID NO:30:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:30:

CACTTACAGG CATA 14

(2) INFORMATION FOR SEQ ID NO:31:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:31:

TATCCCTGTA AGTG 14

( 2 ) INFORMATION FOR SEQ ID NO:32:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:32:

CACTTACAGG GATA         14

( 2 ) INFORMATION FOR SEQ ID NO:33:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:33:

GATCATATTA CTGTAAGTG         19

( 2 ) INFORMATION FOR SEQ ID NO:34:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:34:

GATCCACTTA CAGTAATAT         19

( 2 ) INFORMATION FOR SEQ ID NO:35:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:35:

TATTTCTGTA AGTG         14

( 2 ) INFORMATION FOR SEQ ID NO:36:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:36:

CACTTACAGA AATA 14

( 2 ) INFORMATION FOR SEQ ID NO:37:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:37:

TATTGCTGTA AGTG 14

( 2 ) INFORMATION FOR SEQ ID NO:38:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:38:

CACTTACAGC AATA 14

( 2 ) INFORMATION FOR SEQ ID NO:39:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:39:

TATTCATGTA AGTG 14

( 2 ) INFORMATION FOR SEQ ID NO:40:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:40:

CACTTACATG AATA 14

( 2 ) INFORMATION FOR SEQ ID NO:41:

( i ) SEQUENCE CHARACTERISTICS:
        ( A ) LENGTH: 14 base pairs
        ( B ) TYPE: nucleic acid
        ( C ) STRANDEDNESS: single ( D ) TOPOLOGY: linear ( i i ) MOLECULE TYPE: other nucleic acid
    ( A ) DESCRIPTION: /desc = "OTHER NUCLEIC ACID,
    SYNTHETIC DNA"

( x i ) SEQUENCE DESCRIPTION: SEQ ID NO:41:

TATTCTTGTA AGTG    14

( 2 ) INFORMATION FOR SEQ ID NO:42:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
    SYNTHETIC DNA"

( x i ) SEQUENCE DESCRIPTION: SEQ ID NO:42:

CACTTACAAG AATA    14

( 2 ) INFORMATION FOR SEQ ID NO:43:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
    SYNTHETIC DNA"

( x i ) SEQUENCE DESCRIPTION: SEQ ID NO:43:

TATTCGTGTA AGTG    14

( 2 ) INFORMATION FOR SEQ ID NO:44:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
    SYNTHETIC DNA"

( x i ) SEQUENCE DESCRIPTION: SEQ ID NO:44:

CACTTACACG AATA    14

( 2 ) INFORMATION FOR SEQ ID NO:45:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
    SYNTHETIC DNA"

( x i ) SEQUENCE DESCRIPTION: SEQ ID NO:45:

TATTCCAGTA AGTG    14

( 2 ) INFORMATION FOR SEQ ID NO:46:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:46:

CACTTACTGG AATA     14

(2) INFORMATION FOR SEQ ID NO:47:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:47:

TATTCCGGTA AGTG     14

(2) INFORMATION FOR SEQ ID NO:48:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:48:

CACTTACCGG AATA     14

(2) INFORMATION FOR SEQ ID NO:49:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:49:

GATCATATTC CCGTAAGTG     19

(2) INFORMATION FOR SEQ ID NO:50:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:50:

GATCCACTTA CGGGAATAT                                         19

(2) INFORMATION FOR SEQ ID NO:51:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:51:

GATCATATTC CTATAAGTG                                         19

(2) INFORMATION FOR SEQ ID NO:52:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:52:

GATCCACTTA TAGGAATAT                                         19

(2) INFORMATION FOR SEQ ID NO:53:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:53:

TATTCCTTTA AGTG                                              14

(2) INFORMATION FOR SEQ ID NO:54:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:54:

CACTTAAAGG AATA                                              14

(2) INFORMATION FOR SEQ ID NO:55:

(i) SEQUENCE CHARACTERISTICS:
        (A) LENGTH: 19 base pairs
        (B) TYPE: nucleic acid
        (C) STRANDEDNESS: single
        (D) TOPOLOGY: linear ( i i ) MOLECULE TYPE: other nucleic acid
    ( A ) DESCRIPTION: /desc = "OTHER NUCLEIC ACID,
        SYNTHETIC DNA"

( x i ) SEQUENCE DESCRIPTION: SEQ ID NO:55:

GATCATATTC CTCTAAGTG                                    19

( 2 ) INFORMATION FOR SEQ ID NO:56:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:56:

GATCCACTTA GAGGAATAT                                    19

( 2 ) INFORMATION FOR SEQ ID NO:57:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:57:

TATTCCTGAA AGTG                                         14

( 2 ) INFORMATION FOR SEQ ID NO:58:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:58:

CACTTTCAGG AATA                                         14

( 2 ) INFORMATION FOR SEQ ID NO:59:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:59:

TATTCCTGGA AGTG                                         14

( 2 ) INFORMATION FOR SEQ ID NO:60:

( i ) SEQUENCE CHARACTERISTICS:

( A ) LENGTH: 14 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                SYNTHETIC DNA"

( x i ) SEQUENCE DESCRIPTION: SEQ ID NO:60:

CACTTCCAGG AATA 14

( 2 ) INFORMATION FOR SEQ ID NO:61:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                SYNTHETIC DNA"

( x i ) SEQUENCE DESCRIPTION: SEQ ID NO:61:

TATTCCTGCA AGTG 14

( 2 ) INFORMATION FOR SEQ ID NO:62:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                SYNTHETIC DNA"

( x i ) SEQUENCE DESCRIPTION: SEQ ID NO:62:

CACTTGCAGG AATA 14

( 2 ) INFORMATION FOR SEQ ID NO:63:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                SYNTHETIC DNA"

( x i ) SEQUENCE DESCRIPTION: SEQ ID NO:63:

TATTCCTGTG AGTG 14

( 2 ) INFORMATION FOR SEQ ID NO:64:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                SYNTHETIC DNA"

( x i ) SEQUENCE DESCRIPTION: SEQ ID NO:64:

CACTCACAGG AATA 14

( 2 ) INFORMATION FOR SEQ ID NO:65:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:65:

TATTCCTGTT AGTG    14

( 2 ) INFORMATION FOR SEQ ID NO:66:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:66:

CACTAACAGG AATA    14

( 2 ) INFORMATION FOR SEQ ID NO:67:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:67:

TATTCCTGTC AGTG    14

( 2 ) INFORMATION FOR SEQ ID NO:68:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:68:

CACTGACAGG AATA    14

( 2 ) INFORMATION FOR SEQ ID NO:69:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,

SYNTHETIC DNA"

( x i ) SEQUENCE DESCRIPTION: SEQ ID NO:69:

TATTCCTGTA GGTG　　　　　　　　　　　　　　　　　　　　　　　　　　　　　　　　14

( 2 ) INFORMATION FOR SEQ ID NO:70:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:70:

CACCTACAGG AATA　　　　　　　　　　　　　　　　　　　　　　　　　　　　　　　　14

( 2 ) INFORMATION FOR SEQ ID NO:71:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:71:

TATTCCTGTA TGTG　　　　　　　　　　　　　　　　　　　　　　　　　　　　　　　　14

( 2 ) INFORMATION FOR SEQ ID NO:72:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:72:

CACATACAGG AATA　　　　　　　　　　　　　　　　　　　　　　　　　　　　　　　　14

( 2 ) INFORMATION FOR SEQ ID NO:73:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:73:

TATTCCTGTA CGTG　　　　　　　　　　　　　　　　　　　　　　　　　　　　　　　　14

( 2 ) INFORMATION FOR SEQ ID NO:74:

( i ) SEQUENCE CHARACTERISTICS:
        ( A ) LENGTH: 14 base pairs
        ( B ) TYPE: nucleic acid ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:74:

CACGTACAGG AATA                                                                     14

( 2 ) INFORMATION FOR SEQ ID NO:75:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:75:

GATCATATTC CTGTAAGTG                                                                19

( 2 ) INFORMATION FOR SEQ ID NO:76:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:76:

GATCCACTTA CAGGAATAT                                                                19

( 2 ) INFORMATION FOR SEQ ID NO:77:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:77:

TATTCCTGTA AGT                                                                      13

DNA REGULATORY ELEMENTS RESPONSIVE TO CYTOKINES AND METHODS FOR THEIR USE

This is a continuation-in-part of application(s) Ser. No. 08/228,934 filed Apr. 14, 1994, now abandoned.

FIELD OF THE INVENTION

This invention relates to oligonucleotide sequences that bind regulatory proteins that affect transcription in response to various molecules, such as cytokines, to DNA constructs comprising the oligonucleotide sequences, cells transfected with the DNA constructs, and to methods of using the same to provide for the controlled expression of heterologous genes, for the detection and recovery of new regulatory proteins, and for measuring the ability of compounds to act as agonist and antagonists of gene transcription.

BACKGROUND OF THE INVENTION

In many cellular systems, extracellular signaling molecules, such as polypeptide ligands, bind to receptors on the surface of the cells, thereby triggering an intracellular signaling pathway that ultimately regulates gene transcription within the cells. For example, cytokines and growth factors, which comprise a large and diverse family of soluble polypeptides that control the growth, differentiation and function of mammalian cells, bind to specific cell surface receptors, that in some way transduce signals that elicit a specific phenotypic response. A. Miyajama et al., 10 Annu. Rev. Immunol., 295 (1992); M. Aguet et al., 55 Cell, 273 (1988); T. Kishimoto et al., 258 Science, 593 (1992) and A. Ullrich and J. Schlessinger, 61 Cell, 203 (1990). Abundant evidence shows that changes in the transcription rate of specific genes are an important component of this response. This is thought to be a consequence of alterations in the amount or the activity of specific DNA-binding proteins.

In some instances, progress has been made in defining the pathway that leads from a receptor-ligand interaction at the cell surface to changes in the activity of such DNA binding proteins or other nuclear proteins. Ulrich, 61 Cell 203. In this regard, a common response in surface receptor signaling pathways involves the activation of Ras. L. S. Mulcahy et al., 313 Nature, 241 (1985). Activated Ras then initiates a cascade of serine/threonine phosphorylations through MAP kinases leading to phosphorylation of DNA binding proteins, thereby changing their transcriptional modulatory activity. S. A. Moodie et al., 260 Science, 1658 (1993); C. A. Lange-Carter et al., 260 Science, 315 (1993); C. S. Hill et al., 73 Cell 395 (1993); H. Gille et al., 358 Nature, 414 (1992) and R. H. Chen et al., 12 Mol. Cell. Biol., 915 (1992).

Despite these advances, the signal transduction pathways utilized by many growth factors and cytokines to alter gene expression remain unclear. Thus, although known second messengers have been implicated in signal transduction in response to some of these factors, their role in modulating gene expression remains speculative. Miyajama, 10 Annu. Rev. Immunol., 295 and D. E. Levy and J. E. Darnell, 2 New Biol., 923 (1990). This in turn raises the question of how ligand specific responses are elicited in such cellular systems. Ullrich, 61 Cell, 203; M. V. Chao, 68 Cell, 995 (1992) and Levy, 2 New Biol., 923.

Progress in resolving these issues has been made recently in the interferon (IFN) system. IFNs α and β (type I) act as a primary non-specific defense against viral infections. S. Petska and J. A. Langer, 56 Annu. Rev. Biochem., 727 (1987). IFNγ (type II) has anti-viral properties but also plays a major role in regulation of the immune response. Id. Type I and type II IFNs bind to distinct cell surface receptors and cause rapid alterations in gene expression. Auget, 55 Cell, 273; Uze, 60 Cell, 225; and G. C. Sen and P. Lengyel, 267 J. Biol. Chem., 5017 (1992). Specific sequence elements have been identified in the promoters of genes that respond to IFNα, termed interferon-α stimulated response elements (ISREs), that are both necessary and sufficient for regulation by IFNα. Sen, 267 J. Biol. Chem., 5017. Specifically, activation of the IFNα receptors stimulates tyrosine phosphorylation of a family of proteins that serve as DNA binding proteins, and accordingly as transcription regulatory factors via the ISRE. C. Schindler et al., 257 Science, 809 (1992); K. Shuai et al., 258 Science, 1808 (1992) and M. J. Gutch et al., 89 Proc. Natl. Acad. Sci. USA, 11411 (1992). These DNA binding proteins, generically termed "signal transducers and activators of transcription" (STATs), assemble into a multimeric complex, translocate to the nucleus, and bind cis-acting enhancer elements in the appropriate regulatory regions. D. E. Levy et al., 3 Genes Dev., 1362 (1989); and D. S. Kessler et al., 4 Genes Dev., 1753 (1990) and Z. Zhong et al., 264 Science, 95 (1994).

One example of an IFNα-induced ISRE binding protein complex is ISGF3. T. C. Dale et al., 86 Proc. Natl. Acad. Sci., 1203 (1989) and X-Y. Fu et al., 87 Proc. Natl. Acad. Sci., 8555 (1990). ISGF3 is a complex of 4 binding proteins, called p48, p84 (STAT1β), p91 (STAT1α) and p113 (STAT2). Recently, cDNAs encoding the proteins that constitute ISGF3 have been isolated and characterized. X-Y Fu et al., 89 Proc. Natl. Acad. Sci., 7840 (1992); C. Schindler et al., 89 Proc. Natl. Acad. Sci., 7836 (1992) and S. A. Veals et al., 12 Mol. Cell. Biol. 3315 (1992). p48 is the DNA binding component of ISGF3 and has homology to myb. Veals, 12 Mol. Cell. Biol., 3315. p84 and p91 are probably alternatively spliced products of the same gene and are related to p113. X-Y Fu, 89 Proc. Natl. Acad. Sci., 7840 and Schindler, 89 Proc. Natl. Acad. Sci., 7836. p84, p91 and p113 are novel proteins that contain SH2 and SH3 domains and are found in the cytoplasm of untreated cells. Schindler, 257 Science, 809 and X. Y. Fu, 70 Cell, 323–335 (1992). Thus, IFNα treatment of cells results in rapid tyrosine phosphorylation of p84, p91 and p113, causing them to associate and form a heteromeric complex with p48 to form ISGF3, which then translocates to the nucleus and binds to ISREs, stimulating transcription. Id.; Dale, 86 Proc. Natl. Acad. Sci., 1203 and Kessler, 4 Genes Dev., 1753.

Regulation in response to IFNγ is conferred by a distinct sequence from the ISRE, the gamma activated sequence (GAS). T. Decker et al., 10 EMBO J. 927 (1991); K. D. Khan et al., 90 Proc. Natl. Acad. Sci., 6806 (1993) and D. J. Lew et al., 11 Mol. Cell. Biol., 182 (1991). DNA segments containing just a GAS element can confer an IFNγ response to a heterologous promoter when multimerized Decker et al., 11 Mol. Cell. Biol., 5147–5153 (1991) and Kanno et al., 13 Mol. Cell. Biol., 3951–3963 (1993). Treatment of cells with IFNγ results in tyrosine phosphorylation of p91 (STAT1α), which then forms homodimers that translocate to the nucleus and bind to the GAS element. Decker, 10 EMBO J,. 927; K. Shuai et al., 258 Science, 1808 (1992) and Shuai et al., 76 Cell, 821–828 (1994). Thus the specificity of binding of either IFNα or IFNγ to their receptors is translated into a specific phosphorylation pattern within a related family of latent transcription factors (i.e. DNA binding proteins). This pattern of phosphorylation dictates the association state of the proteins, which determines specificity of binding to either an ISRE or a GAS, and the subsequent transcriptional response.

Yet another cytokine, Interleukin-6 (IL-6) plays a major role in the induction of the acute phase response in hepatocytes. The acute phase response is characterized by the dramatic transcriptional upregulation of a distinct set of genes, termed acute phase response genes. P. C. Heinrich et al., 265 *Biochem. J*, 621–636 (1990). Studies of the promoter regions of these genes have identified specific DNA sequences that are required for induction of acute phase response genes by IL-6. See D. R. Kunz et al., 17 *Nuc. Acids Res.*, 1121–1138 (1989); M. Hattori et al., 87 *Proc. Natl. Acad. Sci USA*, 2364–2368 (1990); K. A. Won and H. Baumann, 10 *Mol. Cell. Biol.*, 3965–3978 (1990) and D. R. Wilson et al., 10 *Mol. Cell. Biol.*, 6181–6191 (1990). These sequences are termed acute phase response elements (APREs). One type of APRE shows many similarities to the GAS elements that confer induction by IFNγ. Several natural GAS elements mediate transcriptional induction by both IFNγ and IL-6. Yuan et al., 14 *Mol. Cell. Biol.*, 1657–1668 (1994); Harroch et al., 13 *EMBO J.*, 1942–1949 (1994) and Harroch et al., 269 *J. Biol. Chem.*, 26191–26195 (1994). Proteins that bind to this class of APREs have been characterized and purified. U. M. Wegenka, et al., 14 *Mol. Cell. Biol.*, 3186–3196 (1994); U. M. Wegenka et al., 13 *Mol. Cell. Biol.*, 276–288 (1993); T. Ito et al., 17 *Nuc. Acids Res.*, 9425–9435 (1989) and Hattori, 87 *Proc. Natl. Acad. Sci. USA*, 2364–2368. A cDNA clone encoding the IL-6-induced APRE-binding protein has been isolated (Zhong, 264 *Science*, 95; Akira et al., 77 *Cell* 63–71 (1994); Zhong, et al., 91 *Proc. Natl. Acad. Sci.*, 4806–4810 (1994); Raz et al., 269 *J. Biol. Chem.*, 24391–24395 (1994)), and was found to encode a protein that shows considerable homology to p91 (STAT1α. For this reason the protein is termed STAT3. Like STAT1α, STAT3 is a latent transcription factor that is activated to bind DNA by rapid tyrosine phosphorylation. In some cells, IL-6 also activates STAT1α. In these cells, heterodimers of STAT1α and STAT3 form in addition to homodimers of STAT1α and homodimers or STAT3. Sadowski et al., 261 *Science*, 1739–1744 (1993); Raz et al., 269 *J. Biol. Chem.*, 24391–24395 (1994) and Zhong et al., 264 *Science*, 95–98 (1994).

Although IFNγ and IL-6 activate STAT proteins that can bind to similar sequences (GAS/APREs), they regulate distinct sets of genes. This suggests that there is specificity with respect to the response elements in some of these genes, such that they respond only to one of these cytokines. In addition, many cytokines other than IFNγ and IL-6 cause the rapid activation of GAS-binding protein complexes. See O. Silvennionen et al., 261 *Science*, 1736 (1993); H. B. Sadowski et al., 261 *Science*, 1739 (1993); A. C. Larner et al., 261 *Science*, 1730 (1993); D. Finbloom et al., 14 *Mol. Cell. Biol.*, 2113–2118 (1994); D. Meyer et al., 269 *J. Biol. Chem.*, 4701–4704 (1994); Lamb, et al., 83 *Blood* 2063–2071 (1994); and Tian, et al., 84 *Blood* 1760–1764 (1994). Some of these complexes contain STAT1α and/or STAT3, and some contain uncharacterized proteins. These cytokines also regulate sets of genes distinct from each other and from those regulated by IFNγ and IL-6. It is therefore possible that distinct classes of GAS-like sequences exist that are selective in their ability to respond to various cytokines. Accordingly, specific DNA sequences that show selectivity with respect to their ability to bind cytokine-activated proteins, including STAT proteins, would be useful tools allowing the responses mediated by different cytokine-activated DNA-binding proteins to be assayed selectively.

The disclosures of the above-cited references are hereby incorporated by reference in their entirety.

SUMMARY OF THE INVENTION

The present invention is directed to oligonucleotide sequences comprising DNA regulatory elements that bind, either directly or indirectly, to activated transcriptional regulatory proteins, preferably STAT proteins, in response to signaling molecules, including cytokines such as interferon gamma (IFNγ), interleukin 4 (IL-4), interleukin 6 (IL-6), and granulocyte-macrophage colony stimulating factor (GM-CSF). Surprisingly, individual point mutations in the Ly6E GAS regulatory element result in discrete regulatory elements that bind a variety of activated transcriptional regulatory proteins and/or specifically bind a single type or class of activated transcriptional regulatory protein. Accordingly, the regulatory elements of the present invention can be used in transcriptional assays to discover agonists or antagonists of a signaling molecule, such as IFNγ, and its cognate transcriptional regulatory protein, STAT1α.

In particular, the present invention provides oligonucleotide sequences comprising regulatory elements of the nucleotide sequence TATTCCTGGAAGT (SEQ ID NO. 1), TATTCCGGTAAGT (SEQ ID NO. 2), TCTTCCTGTAAGT (SEQ ID NO. 3), TATTCTTGTAAGT (SEQ ID NO. 4), TATTCCTGTTAGT (SEQ ID NO. 5), TATTCCCGTAAGT (SEQ ID NO. 6), TATTCCTATAAGT (SEQ ID NO. 7), TATTCCTGTCAGT (SEQ ID NO. 8), TATACCTGTAAGT (SEQ ID NO. 9), TATGCCTGTAAGT (SEQ ID NO. 10), TATTCCTTTAAGT (SEQ ID NO. 11), TATTCCTCTAAGT (SEQ ID NO. 12), TATTCCTGCAAGT (SEQ ID NO. 13), or TATTCCTGTACGT (SEQ ID NO. 14). These oligonucleotide sequences can be double stranded, including their complement.

The present invention also provides a DNA construct comprising the regulatory elements of the oligonucleotide sequences described above operably linked to a promoter, which promoter is operably linked to a heterologous gene, wherein the DNA construct is linked in such a manner that the heterologous gene is under the transcriptional control of the oligonucleotide sequence and promoter. Also provided is a host cell transfected with this DNA construct.

The present invention also provides a method for the controlled expression of a heterologous gene of interest comprising culturing the transfected host cells containing an appropriate transcriptional regulatory protein(s) in the presence of a signaling molecule. Preferably, the signaling molecule in this method comprises a cytokine and the transcriptional regulatory protein comprises a STAT protein.

The present invention further provides a method for detecting the presence of an activated transcriptional regulatory protein, such as a novel STAT protein, in a sample comprising contacting the sample with an oligonucleotide sequence as described above under conditions where the transcriptional regulatory protein is activated and binds with the oligonucleotide sequence to form a complex, and detecting the presence of the complex in the sample. Thereafter, the complex can be separated from the sample, and the transcriptional regulatory protein isolated from the regulatory element.

Further, the present invention provides a method for measuring the ability of a compound to act as an agonist of gene transcription comprising (a) contacting the compound with a transfected host cell as described above under conditions in which the heterologous gene is capable of being expressed in response to the compound, and (b) comparing the level of gene expression in step (a) with the level of gene expression from the host cell in the absence of the compound. Alternatively, the present invention also provides a method for measuring the ability of a compound to act as an antagonist of gene transcription comprising (a) contacting the compound with a transfected host cell as described above in the presence of a predetermined amount of a signaling molecule under conditions in which the heterologous gene is expressed in response to the signaling molecule, and (b) comparing the level of gene expression in step (a) with the level of gene expression from the host cell in the presence of the signaling molecule, but the absence of the compound. In both these methods, the heterologous gene may be any appropriate reporter gene such as the gene for luciferase, chloramphenicol acetyl transferase, green fluorescent protein or β-galactosidase.

Further yet, the present invention provides a method for selectively measuring the ability of a compound to agonize or antagonize the induction of STAT heterodimers comprising (a) contacting the compound with a host cell according to claim 19 under conditions in which the heterologous gene is capable of being expressed in response to the compound, wherein the host cell is transfected with a DNA construct comprising a single copy of an oligonucleotide sequence comprising a regulatory element that that is capable of selectively binding to an activated STAT heterodimer, and (b) comparing the level of gene expression in step (a) with the level of gene expression from the host cell in the absence of the compound.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

DEFINITIONS

For the purposes of this invention:

"Oligonucleotide" or "DNA" molecule or sequence refers to a molecule comprised of the deoxyribonucleotides adenine (A), guanine (G), thymine (T) and/or cytosine (C), in either single-stranded form or a double-stranded helix, and comprises or includes a "regulatory element" according to the present invention, as that term is defined herein. The exact size, strandedness and orientation (i.e. 3' to 5', or 5' to 3') will depend upon many factors, which, in turn, depend upon the ultimate function and use of the oligonucleotides of the present invention. Thus, the term "oligonucleotide" or "DNA" includes double-stranded DNA found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction.

"Regulatory element" refers to a deoxyribonucleotide sequence comprising the whole, or a portion of, an oligonucleotide sequence to which an activated transcriptional regulatory protein, or a complex comprising one or more activated transcriptional regulatory proteins, binds so as to transcriptionally modulate the expression of an associated gene or genes, including heterologous genes.

"Signaling molecule" refers to an extracellular polypeptide, oligosaccharide or other non-peptidyl molecule, in either a free or bound form, that interacts with a receptor at or near the surface of a cell. This interaction in turn triggers an intracellular pathway which includes the activation of one or more transcriptional regulatory proteins that bind to a regulatory element, thereby transcriptionally modulating the expression of an associated gene or genes. As used herein, "signaling molecule" includes naturally occurring molecules, such as cytokines, peptidyl and non-peptidyl hormones, antibodies, cell-surface antigens, or synthetic mimics of any of these signaling molecules, or compounds that mimic the action of any of these signaling molecules.

"Cytokines" refer to a diverse grouping of soluble polypeptides, including growth factors and hormones, that control the growth, differentiation and function of cells in such a manner as to ultimately elicit a phenotypic response in an organism. Preferred cytokines useful with the regulatory elements and associated methods of the present invention include IFNγ, IL-2, IL-3, IL-4, IL-5, IL-6, IL-7, IL-9, IL-10, IL-11, IL-12, IL-13, IL-14, IL-15, Epo, Tpo, GM-CSF, Oncostatin M, growth hormone, G-CSF, LIF, EGF, CNTF and PDGF.

"Transcriptional regulatory protein" refers to cytoplasmic or nuclear proteins that, when activated, bind the regulatory elements/oligonucleotide sequences of the present invention either directly, or indirectly through a complex of transcriptional regulatory proteins or other adapter proteins, to transcriptionally modulate the activity of an associated gene or genes. Thus, transcriptional regulatory proteins can bind directly to the DNA regulatory elements of the present invention, or can bind indirectly to the regulatory elements by binding to another protein, which in turn binds to or is bound to a DNA regulatory element of the present invention. See e.g., S. A. Veals et al., 13 *Molec. Cell. Biol.*, 196–206 (1993). As used herein, transcriptional regulatory proteins, include, but are not limited to, those proteins referred to in the art as STAT proteins (Z. Zhong et al., 264 *Science*, 95) STF proteins (C. Schindler et al., 13 *EMBO J.*, 1350 (1994)), Mammary Gland-Specific Nuclear Factor (M. Schmidt-Ney et al., 6 *Mol. Endochronol.*, 1988 (1992); Wakao, et al., 13 *EMBO J.* 2182–2191 (1994); and H. Wakao et al., 267 *J. Biol. Chem.*, 16365 (1992)), APRF (Wegenka, 13 *Mol. Cell Bio.*, 276), GHIF (Mayer, 269 *J. Biol. Chem.*, 4701); IL-4 STAT (Hou, et al., 265 *Science* 1701–1706 (1994)), GHSF and EPOSF (Finbloom, 14 *Mol. Cell Bio.*, 2113), as well as to all substantially homologous analogs and allelic variations thereof.

"Transcriptionally modulate the expression of an associated gene or genes" means to change the rate of transcription of such gene or genes.

"STAT protein" refers to those transcriptional regulatory proteins designated as "Signal Transducers and Activators of Transcription" (STAT) by Dr. J. E. Darnell of Rockefeller University. See Zhong, 264 *Science* 95. As used herein, STAT proteins include the p91 (STAT1α), p84 (STAT1β), p113 (STAT2) proteins and the STAT-associated p48 family of proteins. S. A. Veals et al., 12 *Mol. Cell. Biol.*, 3315 (1992). Further, STAT proteins also include a binding protein designated as STAT3 (Zhong, et al., 91 *Proc. Natl. Acad. Sci.*, 4806–4810 (1994); Zhong, 264 *Science* 95), and a binding protein designated as STAT4 (Id.). In addition, MGF is now renamed STAT 5 (Gouilleux et al., 13 *EMBO J.* 4361–4369 (1994)), and IL-4-STAT is referred to as STAT6 by some investigators (Ihle et al., 11 *Trends Genet.*, 69 (1995)). Also included are substantially homologous analogs and allelic variations of all of the above STAT proteins.

"Activate", "activated", "activation" or derivatives thereof, means that one or more transcriptional regulatory proteins within a cell are modified post-translationally, or are constituitively active, such that they can bind directly or indirectly to DNA regulatory elements/oligonucleotide sequences of the present invention in a sequence-specific manner. This modification will typically comprises phosphorylation of the transcriptional regulatory proteins via a variety of mechanisms, including, but not limited to activation by various protein kinases. See, e.g. (Shuai, 258 *Science* 1808 and P. Cohen, 17 *TIBS,* 408 (1992)).

"DNA construct" refers to any genetic element, including, but not limited to, plasmids, vectors, chromosomes and viruses, that incorporate the oligonucleotide sequences of the present invention. For example, the DNA construct can be a vector comprising a promoter that is operably linked to an oligonucleotide sequence of the present invention, which is in turn, operably linked to a heterologous gene, such as the gene for the luciferase reporter molecule.

"Promoter" refers to a DNA regulatory region capable of binding directly or indirectly to RNA polymerase in a cell and initiating transcription of a downstream (3' direction) coding sequence. For purposes of the present invention, the promoter is bounded at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain Shine-Dalgarno sequences in addition to the −10 and −35 consensus sequences.

"Gene" refers to a nucleic acid molecule, the sequence of which includes all the information required for the normal regulated production of a particular protein. A "heterologous" region of a DNA construct (i.e. a heterologous gene) is an identifiable segment of DNA within a larger DNA construct that is not found in association with the other genetic components of the construct in nature. Thus, when the heterologous gene encodes a mammalian gene, the gene will usually be flanked by a promoter that does not flank the structural genomic DNA in the genome of the source organism.

A promoter of a DNA construct, including an oligonucleotide sequence according to the present invention, is "operably linked" to a heterologous gene when the presence of the promoter influences transcription from the heterologous gene, including genes for reporter sequences such as luciferase, chloramphenicol acetyl transferase, β-galactosidase and secreted placental alkaline phosphatase. Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

A host cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on an episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA.

"Host cell" refers to a cell line that expresses, either normally or after transfection of the requisite cDNAs, the relevant receptor components for a given signaling molecule, signaling (e.g., kinase) proteins, transcriptional regulatory proteins, and accessory factors such that, upon binding of the signaling molecule to the cell surface, transcriptional regulatory protein-mediated gene transcription is affected. Preferably, the host cell line is responsive to cytokines, such that the host cell line expresses, either normally or after transfection of the requisite cDNAs, the relevant cytokine receptor components, JAK proteins, STAT proteins, and accessory factors such that, upon cytokine binding to the cell surface, STAT-mediated gene transcription is affected.

BRIEF DESCRIPTION OF THE DRAWINGS

The invention may be further illustrated by reference to the accompanying Drawings wherein:

FIG. 1 is a summary of the oligonucleotide competition data for complexes containing transcriptional regulatory proteins activated by IFNγ, IL-6, GM-CSF and IL-4. The wildtype sequence is recited at the top of the figure (SEQ ID No. 77). Each subsequent oligonucleotide is given a designation in the left column consisting of the only nucleotide position which differs from the WT sequence, followed by the nucleotide occurring at the designated position. For example, the oligonucleotide designated 2G differs from the WT sequence by having a G at position 2. The ability of each sequence to compete with the Ly6E GAS element (termed the "wild type, WT" sequence) for binding to transcriptional regulatory proteins activated by either IFN-γ, IL-6, GM-CSF or IL-4 is shown by the number in the appropriate column;

FIG. 5 is a comparison of the in vitro binding affinities of the Ly6E GAS element and the 7C, 8A, 4G, and 8T oligonucleotides containing regulatory elements of the present invention for STAT1α, with the transcriptional induction in response to IFN-γ from constructs containing 4 copies of the same elements. The first column lists the regulatory elements studied. The next column indicates the ability of each element to bind to STAT1α in vitro (data taken from FIG. 1). The last column shows the fold induction of luciferase activity in response to IFN-γ in cells transfected with reporter plasmids containing four copies of the listed regulatory elements.

DETAILED DESCRIPTION OF EMBODIMENTS OF THE INVENTION

Figure 2:
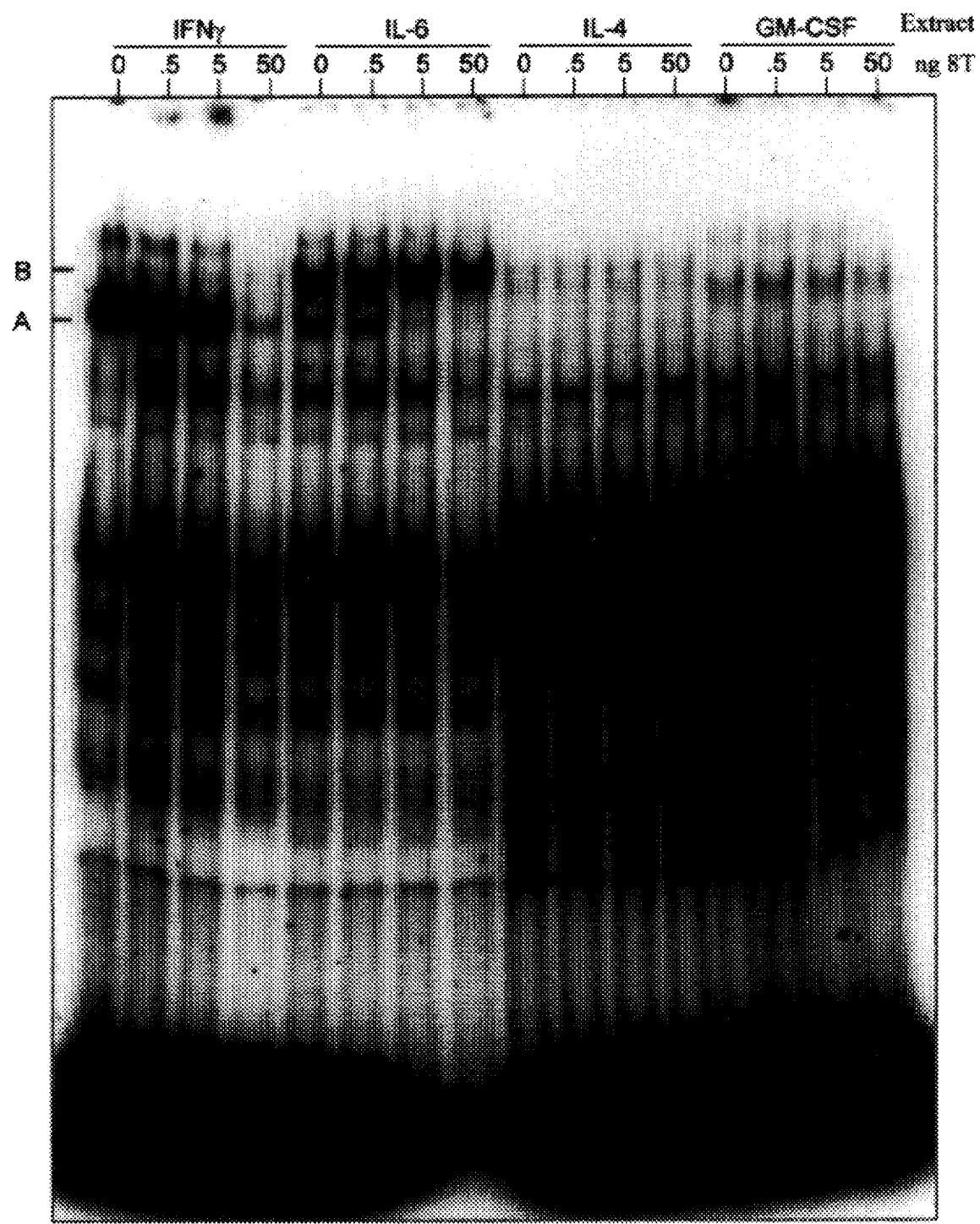
FIG. 2 is an example of an oligonucleotide competition experiment. Nuclear extracts from cells treated with either IFN-γ, IL-6, IL-4 or GM-CSF were incubated with the indicated amounts of oligonucleotide 8T (SEQ ID NO. 11) prior to the addition of radiolabeled Ly6E GAS element probe. Complexes were then separated on a non-denaturing polyacrylamide gel, which was then exposed to X-ray film. A reproduction of the resulting autoradiogram is shown. A and B indicate the positions of the complexes of transcriptional regulatory proteins that correspond to STAT1α and STAT3 respectively.

The present inventors have discovered a series of DNA regulatory elements (i.e. response elements) that in response to various signaling molecules, bind, either directly or indirectly, to activated transcriptional regulatory proteins, and accordingly, transcriptionally modulate the expression of one or more genes operably linked with such regulatory elements. In this regard, the inventors have surprisingly discovered that selected point mutations in the Ly6E GAS response element can transform an element from one that binds with a variety of cytokine-induced, activated transcriptional regulatory proteins to a regulatory element that selectively binds just one type or class of cytokine-induced, activated transcriptional regulatory proteins. For example, the sequence TATACCTGTAAGT (SEQ ID NO. 9) yields a regulatory element that is selective for a STAT1α transcriptional regulatory protein, while the sequence TATTCCCG-TAAGT (SEQ ID NO. 6) yields a regulatory element that is selective for the STAT1α and STAT3 transcriptional regulatory proteins. On the other hand, nucleotide sequences such as TATTCCTGGAAGT (SEQ ID NO. 1) yield a regulatory element that can mediate transcriptional induction in response to a variety of different cytokine-induced transcriptional regulatory proteins, including the STAT1α and STAT3 proteins, as well as those transcriptional regulatory protein(s) that are activated by the IL-4, IL-13 and GM-CSF cytokines.

The regulatory elements according to the present invention are selected from the nucleotide sequences TATTC-CTGGAAGT (SEQ ID NO. 1), TATTCCGGTAAGT (SEQ ID NO. 2), TCTTCCTGTAAGT (SEQ ID NO. 3), TATTCT-TGTAAGT (SEQ ID NO. 4), TATTCCTGTTAGT (SEQ ID NO. 5), TATTCCCGTAAGT (SEQ ID NO. 6), TATTC-CTATAAGT (SEQ ID NO. 7), TATTCCTGTCAGT (SEQ ID NO. 8), TATACCTGTAAGT (SEQ ID NO. 9), TATGC-CTGTAAGT (SEQ ID NO. 10), TATTCCTTTAAGT (SEQ ID NO. 11), TATTCCTCTAAGT (SEQ ID NO. 12), TAT-TCCTGCAAGT (SEQ ID NO. 13), or TATTCCTGTACGT (SEQ ID NO. 14). In this regard, SEQ ID NOs 9-14 comprise STAT1α protein selective regulatory elements, SEQ ID NOs 1-5 comprise regulatory elements that bind a variety of transcriptional regulatory proteins, and SEQ ID NOs 6-8 comprise regulatory elements that selectively bind the STAT1α and STAT3 transcriptional regulatory proteins. Furthermore, these regulatory elements alone, or with additional flanking nucleotide sequences, can form various oligonucleotide sequences according to the present invention. In this regard, it is preferable that such nucleotide sequences comprise between 13 and 200 nucleotides, including the regulatory elements of the present invention. However, sequences in excess of 200 nucleotides that contain the regulatory elements of the present invention, that are capable of binding activated transcriptional regulatory proteins, and of transcriptionally modulating the expression of one or more genes thereby, are considered to be within the scope of the present invention.

The oligonucleotide sequences of the present invention can also comprise multimers of two or more "units" of the basic regulatory elements. In this regard, such multimer oligonucleotide sequences can, as a practical matter, contain from about 2 to 15 units of the same or different regulatory elements according to the present invention. However, theoretically, there is no limit to the number of regulatory elements within such a multimer oligonucleotide sequence. Such multimeric oligonucleotide sequences are useful as probes for detecting, isolating and/or purifying transcriptional regulatory proteins. Further, when used in a DNA construct, including a promoter and heterologous gene, according to the present invention, a multimer of the regulatory elements can enhance the expression of the gene from the DNA construct in response to various cytokines or other signaling molecules.

A variety of signaling molecules activate transcriptional regulatory proteins that bind directly or indirectly to the regulatory elements/oligonucleotide sequences of the present invention. Nonlimiting examples of such signaling molecules include polypeptides such as cytokines and antibodies, and cell-surface antigens, oligosaccarides typically found at or near the surface of cell, non-peptidyl molecules such as TUBag4 (P. Constant et al., 264 *Science*, 267 (1994)) and synthetic mimics any of these molecules, in both their free and bound forms. Thus, the present invention includes cell to cell or cell to substrate transcriptional regulatory protein activation via signaling molecules bound to or near the surface of a cell or other substrate.

Preferably, the signaling molecules according to the present invention comprise cytokines that activate transcriptional regulatory proteins that bind to the regulatory elements/oligonucleotide sequences of the present invention. Examples of such cytokines include, but are not limited to, Interleukins 2, 3, 4, 5, 6, 7, 9, 10, 11, 12, 13 and 15 (IL-2, IL-3, IL-4, IL-5, IL-6, IL-7, IL-9, IL-10, IL-11, IL-12, IL-13 and IL-15), granulocyte-macrophage colony stimulating factor (GM-CSF), granuloctyte colony stimulating factor (G-CSF), colony stimulating factor 1 (CSF-1), interferons alpha, beta, and gamma (IFNα, IFNβ, IFNγ), epidermal growth factor (EGF), platelet derived growth factor (PDGF), leukemia inhibitory factor (LIF), Oncostatin-M, nerve growth factor (NGF), ciliary neurotrophic factor (CNTF), brain-derived neurotrophic factor (BDNF), erythropoietin (Epo), thrombopoietin (Tpo), growth hormone and prolactin. Particularly preferred cytokines according to the present invention include, but are not limited to, IFNγ, IL-4, IL-6, GM-CSF, Oncostatin-M, G-CSF, LIF, EGF, PDGF, Epo, Tpo and CNTF.

The regulatory elements and/or oligonucleotide sequences of the present invention will also prove useful in detecting, isolating and purifying new transcriptional regulatory proteins that display binding specificity to the regulatory elements/oligonucleotide sequences of the present invention. Further, it is contemplated that these regulatory elements/oligonucleotide sequences will prove particularly useful in the discovery of novel STAT proteins or STAT-related transcriptional regulatory proteins. In this regard, detection of such novel transcriptional regulatory proteins can be accomplished with the following technique. Cells, such as HepG2 cells, are treated with an appropriate cytokine, for example, with IFNγ for 15 minutes to induce the activation of one or more transcriptional regulatory proteins. Extracts of the nucleus and cytoplasm of these cells are then prepared using conventional methods and tested for binding to the regulatory elements/oligonucleotide sequences by an electrophoretic mobility shift assay, in comparison with untreated cells that will show little or no specific binding as described in Levy, 3 *Genes Dev.*, 1362 and Kessler, 4 Genes Dev., 1753, the disclosures of which are herein incorporated by reference. Furthermore, DNA regulatory element binding activity may also be stimulated in vitro by treating a cytoplasmic extract, supplemented with cell membranes, with a signaling molecule, such as cytokine.

If an antibody specific for a transcriptional regulatory protein is available, it can be used to specifically interfere with the binding of the regulatory element of the present invention to the activated transcriptional regulatory protein, thereby assisting in the identification of the transcriptional regulatory protein. Furthermore, an unknown transcriptional regulatory protein identified or purified using the regulatory elements/oligonucleotide sequences of the present invention can be used to immunize animals to prepare an antibody specific for the transcriptional regulatory protein using methods well known in the art. See, e.g., E. Harlow, et al., Antibodies: A Laboratory Manual, Cold Spring Harbor Laboratory Press, Cold Spring Harbor, N.Y. (1988), the disclosure of which is herein incorporated by reference.

Thus, the regulatory elements/nucleotide sequences of the present invention thus can serve as a "probe", similar to those used in a variety of nucleic acid detection systems well known in the art, except that the probes of the present invention are used to detect proteins, rather than a nucleic acid sequences, which specifically bind to the regulatory elements/oligonucleotide sequences of the present invention.

The sensitivity of such a nucleic acid detection assay can be increased by altering the manner in which a signal is detected by an observer. For example, assay sensitivity can be increased through the use of labeled oligonucleotide sequences using a wide variety of detectable labels, including, without limitation, enzyme labels, radioisotopic labels, fluorescent labels, and modified bases. See, e.g., U.S. Pat. Nos. 4,581,333, 4,358,535, 4,446,237, 4,582,789, and 4,563,417, as well as European Patent Application Nos. EP 144914 and EP 119448, the disclosures of which are herein incorporated by reference. Thus, DNA probes according to the present invention preferably include the regulatory elements alone, or as part of a longer oligonucleotide sequence of the present invention, labeled with a detectable label, such as a radioisotope, an enzyme, a fluorescent label, a chemical label, or a modified base.

Thus, the present invention provides a method for detecting the presence of novel transcriptional regulatory proteins in a sample. Such samples are preferably biological samples, including, but not limited to, cells, cell culture supernatant, cell or tissue extracts, or particular fractions thereof, and other biological fluids such as blood, sera, urine, saliva, etc. Binding of the probe containing the regulatory elements/ oligonucleotide sequences of the present invention to a transcriptional regulatory protein in the sample may be detected by any appropriate means known in the art. For example, direct or indirect, or competitive binding assays may be used. In such assays, association of the labeled probe with the proteinaceous material of the sample is then detected. In a preferred embodiment, the oligonucleotide sequence is modified by the incorporation of a radioactivity labeled nucleotide.

Once detected, the novel transcriptional regulatory protein can be separated and purified from the probe-protein complex by any of a variety of techniques well known to those of skill in the art. For example, such isolation and purification can be based on affinity chromatography, which relies on the interaction of the protein to be purified with an immobilized ligand. In the present invention, a regulatory element and/or oligonucleotide sequence of the present invention immobilized on a support would serve as the immobilized ligand, which in turn would be used to isolate and purify a novel transcriptional regulatory protein from a sample.

In a preferred embodiment, the regulatory element/ oligonucleotide sequence of the present invention is immobilized on a solid support or carrier. As used herein "solid phase carrier or support" refers to any support capable of binding the oligonucleotide sequences/DNA regulatory elements of the present invention. Well known supports, or carriers, include glass, polystyrene, polypropylene, polyethylene, dextran, nylon, amyloses, natural and modified celluloses, polyacrylamides, agaroses, and magnetite. Methods for coupling nucleic acids to the solid phase, the solid phase substances useful in these methods, and the means for elution of the proteins from the bound ligand, are well known to those of skill in the art.

In addition to the specific methods described above, purification steps prior to affinity separation may also include one or more additional methods, such as ammonium sulfate precipitation, size exclusion chromatography (gel filtration), ion exchange chromatography, differential precipitation and the like, all well known in the art. Also useful is the method known as hydrophobic interaction chromatography (HIC) which is based on the interaction between the solute and the gel that is hydrophobic. Hydrophobic interactions are strongest at high ionic strength, therefore, this form of separation is conveniently performed following salt precipitations or ion exchange procedures. Elution from HIC supports can be effected by alterations in solvent, pH, ionic strength, or by the addition of chaotropic agents or organic modifiers, such as ethylene glycol. General principles of HIC are described in U.S. Pat. Nos. 3,917,527 and 4,000,098. Purification of specific proteins using HIC is described in the U.S. Pat. Nos.: 4,332,717; 4,771,128; 4,743,680; 4,894,439; 4,908,434; and 4,920,196, the disclosures of which are herein incorporated by reference.

The regulatory elements/oligonucleotide sequences of the present invention may be included in a recombinant DNA construct which contains a regulatory element/ oligonucleotide sequence operably linked to a promoter and a heterologous gene. Typically the heterologous gene comprises a reporter sequence, such as the gene for luciferase. In this regard, a recombinant DNA construct, such as a reporter plasmid according to the present invention, can be constructed using conventional molecular biology, microbiology, and recombinant DNA techniques well known to those skill in the art. Such techniques are explained fully in the literature, including Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins, eds. (1984)]; "Animal Cell Culture" [R. I. Freshney, ed. (1986)]; "Immobilized Cells and Enzymes" [IRL Press, (1986)] and B. Perbal, "A Practical Guide to Molecular Cloning" (1984), the disclosures of which are herein incorporated by reference.

Promoter sequences useful in DNA constructs according to the present invention include all prokaryotic, eukaryotic or viral promoters capable of driving transcription of a heterologous gene of interest in combination with a regulatory element of the present invention, when transfected into an appropriate host cell. Suitable prokaryotic promoters include, but are not limited to, promoters recognized by the T4, T3, Sp6, and T7 polymerases, the $P_R$ and $P_L$ promoters of bacteriophage λ, the transcriptional regulatory protein, recA, heat shock, and lacZ promoters of E. coli, the α-amylase and the σ-28-specific promoters of B. subtilis, the promoters of the bacteriophages of Bacillus, Streptomyces promoters, the int promoter of bacteriophage λ, the bla promoter of the β-lactamase gene of pBR322 and the CAT promoter of the chloramphenicol acetyl transferase gene of pPR325. See, e.g., B. R. Glick, 1 J. Ind. Microbiol., 277–282 (1987); Y. Cenatiempo, 68 Biochimie, 505–516 (1986); J. D. Watson et al., In: Molecular Biology of the Gene, Fourth Edition, Benjamin Cummins, Menlo Park, Calif. (1987) and S. Gottesman, 18 Ann. Rev. Genet., 415–442 (1984), the disclosures of which are herein incorporated by reference. Preferred eukaryotic promoters include the yeast cyc-1 promoter, the promoter of the mouse metallothionein I gene, the thymidine kinase promoter of the Herpes simplex virus, the SV40 early promoter, and the yeast gal-4 gene promoter. See Guarante et al., 78 Proc. Natl. Acad. Sci. USA, 2199–2203 (1981), D. Hamer et al., 1 J. Mol. Appl. Gen., 273–288 (1982), S. McKnight, 31 Cell, 355–365 (1982), C. Benoist et al., 290 Nature (London), 304–310 (1981), S. A. Johnston et al., 79 Proc Natl. Acad. Sci. (USA), 6971–6975 (1982) and P. A. Silver et al., 81 Proc. Natl. Acad. Sci. (USA), 5951–5955 (1984), the disclosures of which are herein incorporated by reference herein. Preferably, a DNA construct according to the present invention utilizes the thymidine kinase gene promoter of the Herpes simplex virus.

The third component of the recombinant DNA or construct molecules of the present invention is a "heterologous gene" which may be composed of any set of. nucleotides regardless of sequence. Nonlimiting examples of such heterologous genes include the structural genes for luciferase, β-galactosidase, chloramphenicol acetyl transferase, secreted placental alkaline phosphatase, human growth hormone, tPA and inteferon. For a more extensive list of heterologous genes usable in the constructs and methods of the present invention, see Beaudet, 37 Am. J. Hum. Gen., 386–406 (1985).

Preferably the heterologous gene comprises a reporter gene whose product is used to assess regulation of transcription via a promoter and a regulatory element/oligonucleotide sequence of the present invention. The expression of this "reporter sequence" results in the formation of a reporter product (e.g., protein) which is readily detectable. The reporter sequence will preferably be selected such that the reporter molecule will have a physical and chemical characteristics which will permit or facilitate its identification or detection by means well known in the art. In one embodiment, the presence of the reporter molecule will be detected through the use of an antibody or an antibody fragment, capable of specific binding to the reporter molecule. In another embodiment, a reporter such as β-galactosidase or luciferase can be assayed enzymatically or immunologically.

A preferred reporter molecule is LUC, well known in the art. Sees e.g., J. R. De-Wet et al., 7 Mol. Cell Bio., 725 (1987). Because this is an insect gene, it is absent from mammalian cells and the enzyme product can be directly assayed in a cell extract. The level of enzyme activity corresponds to the amount of enzyme that was made, which in turn reveals the level of expression. In addition, LUC mRNA may also be measured directly.

Typically, a plasmid containing the recombinant DNA molecule of the present invention, including the LUC gene, is introduced into mammalian cells, which are then grown to, at or near confluency. In this regard, any host cell capable of activating one or more transcriptional regulatory proteins in response to an appropriate signaling molecule or molecules can be transfected with the DNA constructs of the present invention. Preferably, such host cells comprise mammalian cells, such as HepG2 and U937 cells (available from ATCC, Rockville, Md.).

The reporter cells are treated with a compound or sample suspected of containing a signaling molecule capable of inducing or activating a transcriptional regulatory protein, for example, a medium that has been in contact with cells suspected of producing a signaling molecule, such as a cytokine. The LUC-producing reporter cells are extracted, and the soluble extracts are supplemented with luciferin and ATP. In the presence of these compounds the action of luciferase generates light, which is detected using a luminometer. The amount of light produced is directly related to the amount of luciferase present in the cellular extract.

With a suitable DNA construct transfected into a host cell, the present invention provides a method for the controlled expression of a gene of interest. Thus, application of a signaling molecule, such as cytokine, to transfected host cells can be used to drive the expression of a heterologous gene to yield defined quantities of a desired product, such as human growth hormone, by any of a variety of cell culture and fermentation techniques well known to those of skill in the art.

Alternatively, when the DNA construct comprises a reporter sequence, such as the gene for luciferase, transfection of the DNA construct into a host cell provides a convenient means for measuring the transcriptional activity of a reporter product in response to a signaling molecule, such as a cytokine or a medium that has been in contact with cells suspected of producing a signaling molecule, such as a cytokine.

Importantly, when transcription of LUG is activated by the transcriptional regulatory protein being assayed, LUC synthesis is increased relative to a control lacking the transcriptional regulatory protein. Thus, the amount of LUC enzyme produced is an indirect measure of transcription induced by the activated transcriptional regulatory protein binding to the regulatory elements/oligonucleotide sequences of the present invention, which is operably linked to the LUC gene.

When a preferred host cell, such as a HepG2 cell, is transfected with a reporter DNA construct according to the present invention, it can be utilized in assays to detect agonists and antagonists of signaling molecules that induce gene transcription via activated transcriptional regulatory proteins. As used herein, agonists or antagonist of gene transcription include compounds that intervene at any point with in the signaling pathway from interaction between the signaling molecule and a cell surface receptor through activation of one or more transcriptional regulatory proteins and binding of the same to DNA regulatory elements, the end remit of which is modulation of gene transcription. Further, as used herein, agonists and antagonists of gene transcription also include potentiators of known compounds with such agonist or antagonist properties. Agonists can be detected by contacting the transfected host cell with a compound or mix of compounds and, after a fixed period of time, determining the level of gene expression (e.g., the level of luciferase produced) within the treated cells. This expression level can then be compared to the expression level of the reporter gene in the absence of the compound(s). The difference between the levels of gene expression, if any, indicated whether the compound(s) of interest agonize the activation of intracellular transcriptional regulatory proteins in an analogous fashion to a known agonist signaling molecule, such as a cytokine. Further, the magnitude of the level of reporter product expressed between the treated and untreated cells provides a relative indication of the strength of that compound(s) as an agonist of gene transcription via a transcriptional regulatory protein pathway.

Alternatively, such a transfected host cell can be used to find antagonists of known agonists, e.g., cytokines such as IFNγ, of gene transcription utilizing host cells transfected with the DNA constructs according to the present invention. In such an assay, the compound or compounds of interest are contacted with the host cell in conjunction with one or more known agonists (e.g., cytokines) held at a fixed concentration. The extent to which the compound(s) depress the level of gene expression in the host cell below that available from the host cell in the absence of compounds, but presence of the known agonist, provides an indication and relative strength of the antagonist properties of such compound(s).

Thus, the present invention provides methods to assay for agonists and antagonists of gene transcription utilizing the regulatory elements/oligonucleotides of the present invention in appropriate DNA constructs and transfected host cells. In addition, the present invention provides a unique selective assay for agonists and antagonists of STAT heterodimer pathways, including the STAT1α/STAT3 heterodimer pathway. Further, the agonist and antagonist compounds discovered utilizing these methods can serve as pharmaceutical agents in the intervention of various cytokine-induced disease states and conditions, or to ameliorate disease states caused by cytokine deficiency, such as intimation, infection, anemia, cytopenia and cancerous or precancerous conditions.

The invention will be further illustrated by reference to the following non-limiting Examples.

EXAMPLE 1

In order to determine the relative affinities of the regulatory elements of the present invention for different cytokine-activated DNA-binding proteins, the following experiment was performed. Nuclear extracts from cells treated with either interferon-γ (IFNγ), IL-6, IL-4 or GM-CSF were incubated with various concentrations of unlabeled competitor DNA (i.e. potential regulatory elements/oligonucleotide sequences of the present invention: the "test" sequence) prior to the addition of radiolabeled DNA consisting of the Ly6E GAS element. Cytokine-induced GAS-binding complexes were then resolved on non-denaturing polyacylamide gels, which were then subject to autoradiography. The ability of a "test" sequence to compete with the labeled Ly6E GAS element for the binding of a particular cytokine-induced complex was assessed by the reduction in the intensity of the band in the autoradiographs representing the cytokine-induced complex. See e.g., FIG. 2. Details of these experiments are given below.

HepG2 cells (obtained from the American Type Culture Collection, Rockville Md.) were grown in Dulbecco's modified Eagle's medium (Bio Whittaker, Walkersville, Md.)) containing 2 mM glutamine, 10% fetal calf serum and 100 U/ml penicillin and streptomycin on 90 mm tissue culture dishes. Cells were treated with 5 ng/ml human interferon-γ (J. Darnell, Rockefeller University New York N.Y.: commercially available from Genzyme, Cambridge, Mass.) or 20 ng/ml human IL-6 (R&D Systems, Minneapolis, Minn.) for 15 minutes when the cells had reached 70% confluency. U937 cells (J. Darnell, Rockefeller University New York N.Y.: commercially available from ATCC) were grown in RPMI medium (BioWhittaker) containing 2 mM glutamine, 10% fetal calf serum and 100 U/ml penicillin and streptomycin in 75 cm$^2$ tissue culture flasks. Cells were treated with 20 ng/ml human IL-4 or 10 ng/ml human GM-CSF (both from R&D Systems, Minneapolis, Minn.) for 30 minutes when the cells were at a density of 2–5×10$^5$ cells/ml.

Nuclear extracts were prepared by NP40 lysis as described in H. B. Sadowski and M. Z. Gilman, 362 *Nature*, 79 (1993), the disclosure of which is herein incorporated by reference. Protein concentrations were measured using the Bradford dye binding assay (BioRad Laboratories, Hercules, Calif.). The GAS oligonucleotide based on an IFNγ responsive element in the Ly6E gene promoter (K. D. Khan et al., 90 *Proc. Natl. Acad. Sci.*, 6806, (1993)), was formed by annealing oligonucleotides with the sequences:

| 5' | GATCATATTCCTGTAAGTG | 3' | SEQ ID NO. 75 |
|---|---|---|---|
| 3' | TATAAGGACATTCACCTAG | 5' | SEQ ID NO. 76 |

Further, the double-stranded probe oligonucleotides, incorporating the regulatory elements of the present invention, used in the Electrophoretic Mobility Shift Assays (EMSAs) were formed by annealing oligonucleotides with the sequences:

| 5' | TTTTCCTGTAAGTG | 3' | SEQ ID NO. 15 |
|---|---|---|---|
| 3' | AAAAGGACATTCAC | 5' | SEQ ID NO. 16 |
| 5' | TGTTCCTGTAAGTG | 3' | SEQ ID NO. 17 |
| 3' | ACAAGGACATTCAC | 5' | SEQ ID NO. 18 |
| 5' | TCTTCCTGTAAGTG | 3' | SEQ ID NO. 19 |
| 3' | AGAAGGACATTCAC | 5' | SEQ ID NO. 20 |
| 5' | TAATCCTGTAAGTG | 3' | SEQ ID NO. 21 |
| 3' | ATTAGGACATTCAC | 5' | SEQ ID NO. 22 |
| 5' | GATCATAGTCCTGTAAGTG | 3' | SEQ ID NO. 23 |
| 3' | TATCAGGACATTCACCTAG | 5' | SEQ ID NO. 24 |
| 5' | GATCATACTCCTGTAAGTG | 3' | SEQ ID NO. 25 |
| 3' | TATGAGGACATTCACCTAG | 5' | SEQ ID NO. 26 |
| 5' | TATACCTGTAAGTG | 3' | SEQ ID NO. 27 |
| 3' | ATATGGACATTCAC | 5' | SEQ ID NO. 28 |
| 5' | TATGCCTGTAAGTG | 3' | SEQ ID NO. 29 |
| 3' | ATACGGACATTCAC | 5' | SEQ ID NO. 30 |
| 5' | TATCCCTGTAAGTG | 3' | SEQ ID NO. 31 |
| 3' | ATAGGGACATTCAC | 5' | SEQ ID NO. 32 |
| 5' | GATCATATTACTGTAAGTG | 3' | SEQ ID NO. 33 |
| 3' | TATAATGACATTCACCTAG | 5' | SEQ ID NO. 34 |
| 5' | TATTTCTGTAAGTG | 3' | SEQ ID NO. 35 |
| 3' | ATAAAGACATTCAC | 5' | SEQ ID NO. 36 |
| 5' | TATTGCTGTAAGTG | 3' | SEQ ID NO. 37 |
| 3' | ATAACGACATTCAC | 5' | SEQ ID NO. 38 |
| 5' | TATTCATGTAAGTG | 3' | SEQ ID NO. 39 |
| 3' | ATAAGTACATTCAC | 5' | SEQ ID NO. 40 |
| 5' | TATTCTTGTAAGTG | 3' | SEQ ID NO. 41 |
| 3' | ATAAGAACATTCAC | 5' | SEQ ID NO. 42 |
| 5' | TATTCGTGTAAGTG | 3' | SEQ ID NO. 43 |
| 3' | ATAAGCACATTCAC | 5' | SEQ ID NO. 44 |
| 5' | TATTCCAGTAAGTG | 3' | SEQ ID NO. 45 |
| 3' | ATAAGGTCATTCAC | 5' | SEQ ID NO. 46 |
| 5' | TATTCCGGTAAGTG | 3' | SEQ ID NO. 47 |
| 3' | ATAAGGCCATTCAC | 5' | SEQ ID NO. 48 |
| 5' | GATCATATTCCCGTAAGTG | 3' | SEQ ID NO. 49 |
| 3' | TATAAGGGCATTCACCTAG | 5' | SEQ ID NO. 50 |

-continued

| 5' | GATCATATTCCTATAAGTG | 3' | SEQ ID NO. 51 |
| 3' | TATAAGGATATTCACCTAG | 5' | SEQ ID NO. 52 |
| 5' | TATTCCTTTAAGTG | 3' | SEQ ID NO. 53 |
| 3' | ATAAGGAAATTCAC | 5' | SEQ ID NO. 54 |
| 5' | GATCATATTCCTCTAAGTG | 3' | SEQ ID NO. 55 |
| 3' | TATAAGGAGATTCACCTAG | 5' | SEQ ID NO. 56 |
| 5' | TATTCCTGAAAGTG | 3' | SEQ ID NO. 57 |
| 3' | ATAAGGACTTTCAC | 5' | SEQ ID NO. 58 |
| 5' | TATTCCTGGAAGTG | 3' | SEQ ID NO. 59 |
| 3' | ATAAGGACCTTCAC | 5' | SEQ ID NO. 60 |
| 5' | TATTCCTGCAAGTG | 3' | SEQ ID NO. 61 |
| 3' | ATAAGGACGTTCAC | 5' | SEQ ID NO. 62 |
| 5' | TATTCCTGTGAGTG | 3' | SEQ ID NO. 63 |
| 3' | ATAAGGACACTCAC | 5' | SEQ ID NO. 64 |
| 5' | TATTCCTGTTAGTG | 3' | SEQ ID NO. 65 |
| 3' | ATAAGGACAATCAC | 5' | SEQ ID NO. 66 |
| 5' | TATTCCTGTCAGTG | 3' | SEQ ID NO. 67 |
| 3' | ATAAGGACAGTCAC | 5' | SEQ ID NO. 68 |
| 5' | TATTCCTGTAGGTG | 3' | SEQ ID NO. 69 |
| 3' | ATAAGGACATCCAC | 5' | SEQ ID NO. 70 |
| 5' | TATTCCTGTATGTG | 3' | SEQ ID NO. 71 |
| 3' | ATAAGGACATACAC | 5' | SEQ ID NO. 72 |
| 5' | TATTCCTGTACGTG | 3' | SEQ ID NO. 73 |
| 3' | ATAAGGACATGCAC | 5' | SEQ ID NO. 74 | where the nucleotide sequences shown in bold face type correspond to the nucleotide sequences, including their double stranded complement, tested for activity as regulatory elements according to the present invention.

The annealed oligonucleotides were labeled by filling in the overhanging ends with Klenow fragment (Boehringer Mannheim) in the presence of [α$^{32}$P]- dGTP or dATP (Amersham Corporation, Arlington Heights, Ill.). Oligonucleotides were purchased from National Biosciences (Plymouth Minn.) or Integrated DNA Technologies (Coralville, Iowa). EMSAs were performed in 13 mM HEPES buffer (Sigma Chemical, St. Louis, Mo.) (pH 7.6), 80 mM sodium chloride, 3 mM sodium fluoride, 3 mM sodium molybdate, 1 mM DTT, 0.15 mM EDTA, 0.15 mM EGTA and 8% glycerol (including contributions from the nuclear extract) and contained 75 µg/ml poly d(I-C) poly d(I-C), approximately 0.2 ng of radiolabeled Ly6E GAS element, either 0.5, 5.0 or 50.0 ng of competition sequence and 10–15 µg of protein. Reactions containing all components except the radiolabeled Ly6E GAS element were incubated on ice for 10 minutes, followed by a further 20 minute incubation at room temperature following the addition of radiolabeled Ly6E GAS element. Reactions were then resolved on 5% polyacrylamide gels containing 0.25× TBE (1× TBE is 89 mM Tris borate, 1 mM EDTA [pH 8.0]) and 5% glycerol. Gels were run at 4° C. in 0.25× TBE at 20 V/cm, then dried and autoradiographed.

The ability of each "test" oligonucleotide (SEQ ID NOs. 15–74) to compete for the binding of the Ly6E GAS element to the DNA-transcriptional regulatory protein binding complexes induced by IFNγ, IL-6, IL-4 and GM-CSF were visually rated and scored according to the following scale:

0 No competition evident

1 Less than 50% reduction in intensity of the band corresponding to specific complex seen with 50 ng of competitor.

2 Greater than 50% reduction in intensity of the band corresponding to specific complex seen with 50 ng of competitor.

3 Less than 50% reduction in intensity of the band corresponding to specific complex seen with 5 ng of competitor.

4 Greater than 50% reduction in intensity of the band corresponding to specific complex seen with 5 ng of competitor.

5 Less than 50% reduction in intensity of the band corresponding to specific complex seen with 0.5 ng of competitor.

6 Greater than 50% reduction in intensity of the band corresponding to specific complex seen with 0.5 ng of competitor.

Thus higher numbers indicate a greater ability to compete for particular complexes that comprise or include transcriptional regulatory proteins. Numbers were assigned by visual inspection of the autoradiograms by two independent scientists, and differences in ratings resolved by consensus. If desired, the use of a phosphoimager or densitometer (commercially available from e.g. Bio-Rad Laboratories) could provide a means to assess the differences described here quantitatively. The specific visual ratings of binding affinities for the regulatory elements of oligonucleotide SEQ ID NOs. 15–74 are shown in FIG. 1. In this regard, when interpreting the results shown in FIG. 1, the data should be analyzed for trends as opposed to specific numerical values. This is due to the inherent lack of fine sensitivity in the EMSA assay. This variability can arise, at least in part, from differences in the quality of nuclear extracts used, cell line differences, and variability in the protein concentration determinations.

An example of an autoradiograph of an EMSA used to generate the data in FIG. 1 is shown in FIG. 2. In particular, FIG. 2 shows the ability of oligonucleotide sequence 8T (SEQ ID NO. 53–54) to compete for specific cytokine-activated transcriptional regulatory protein complexes. In evaluating these FIGS., one should be aware that IL-6 induces 3 specific DNA-binding complexes in HepG2 cells. P. Lamb et al., 83 *Blood* 2063 (1994). Accordingly, for the column marked IL-6, the complex being rated is the slowest-migrating IL-6 induced complex whose position is indicated by the "B" in FIG. 2, and which consists of a homodimer of STAT3 (Z. Zhong et al., 264 *Science*, 95 (1994); Raz, et al., 269 *J. Biol. Chem.* 24391–24391 (1994)), and thus is not reflective of complexes that contain STAT1α (p91), which is rated in the IFNγ complex.

Analysis of the data in FIG. 1 shows that point mutations in various positions within the Ly6E GAS element profoundly effect the ability of the resulting sequences to bind to cytokine-activated transcriptional regulatory proteins. Some of the mutations eliminate or drastically weaken binding to the transcriptional regulatory proteins activated by IFN-γ, IL-6, GM-CSF and IL-4. Other mutations result in sequences that bind more tightly to these proteins than to the native Ly6E GAS (e.g., WT) sequence, for example sequence 9G, (SEQ ID NO. 59–60). Surprisingly, some mutations selectively alter the ability of the resulting sequences to bind to cytokine-activated transcriptional regulatory proteins. These sequences fall into 2 classes; those that bind to the IFN-γ activated protein STAT1α, but not to the proteins activated by IL-6, GM-CSF or IL-4, and those that bind to the IFN-γ activated proteins STAT1α and to the IL-6 activated protein STAT3, but not to the proteins activated by GM-CSF and IL-4. An example of the former class of sequences is sequence 8T (SEQ ID NO. 53–54), and of the latter class is sequence 7C (SEQ ID NO. 49–50).

The remarkable selectivity of sequence 8T is demonstrated in FIG. 2. This sequence competes for binding to the STAT1α complex induced by IFN-γ (indicated by the "A" in FIG. 2), as evidenced by the reduction in the intensity of this band as increasing amounts of 8T are added to the reaction. However, the STAT3 complex induced by IL-6 (labeled "B" in FIG. 2) and the complexes induced by GM-CSF and IL-4 are unaffected by the presence of this sequence. Note that IL-6 induces a small amount of STAT1α in HepG2 cells (P. Lamb et al., 83 *Blood* 2063), and this complex is also reduced in intensity by the addition of sequence 8T.

The selectivity demonstrated by the sequences that bind only to the IFN-γ activated proteins (STAT1α) or to both the IFN-γ and IL-6 activated proteins (STAT1α and STAT3) will hold true for other signaling molecules that activate STAT1 and/or STAT3, such as growth hormone, G-CSF, LIF, Oncostatin M, CNTF, EGF, PDGF, IL-11 and IL-10.

EXAMPLE 2

In order to determine the ability of the Ly6E GAS element and regulatory elements of the present invention to mediate transcriptional induction in response to test cytokines, reporter plasmids were constructed by cloning the regulatory elements into a modified pZLUC plasmid that contains the HSV TK promoter from −35 to +10 as described in Shuai et al., 261 *Science*, 1744–1746 (1993), the disclosure of which is herein incorporated by reference. HepG2 cells were transfected by calcium phosphate coprecipitation. Cells were seeded at 2×10$^5$/ml the day before transfection. Cells were exposed to a calcium phosphate precipitate containing 15 μg/ml of the above-described reporters and 5 μg/ml of the β-galactosidase expressing plasmid pCH110 for 5 hours. When included, STAT1α (Shuai et al., 1993), STAT3 (Zhong et al., 1994) or empty expression vectors were present at 10 μg/ml. The medium was then changed and the cells allowed to recover for 16 hours. Recombinant cytokines were then added directly to the medium (IFN-γ, 5 ng/ml; IL-6, 10 ng/ml; LIF 10 ng/ml and OSM 10 ng/ml) and the cells harvested 5 hours later. Cells were lysed and luciferase and β-galactosidase activities determined using standard techniques. For each sample the normalized response was determined by dividing relative light units obtained from the luciferase assay with the β-galactosidase activity in the same lysate as determined using a chromogenic substrate. Each point represents the average normalized response from three experiments.

Figure 3:
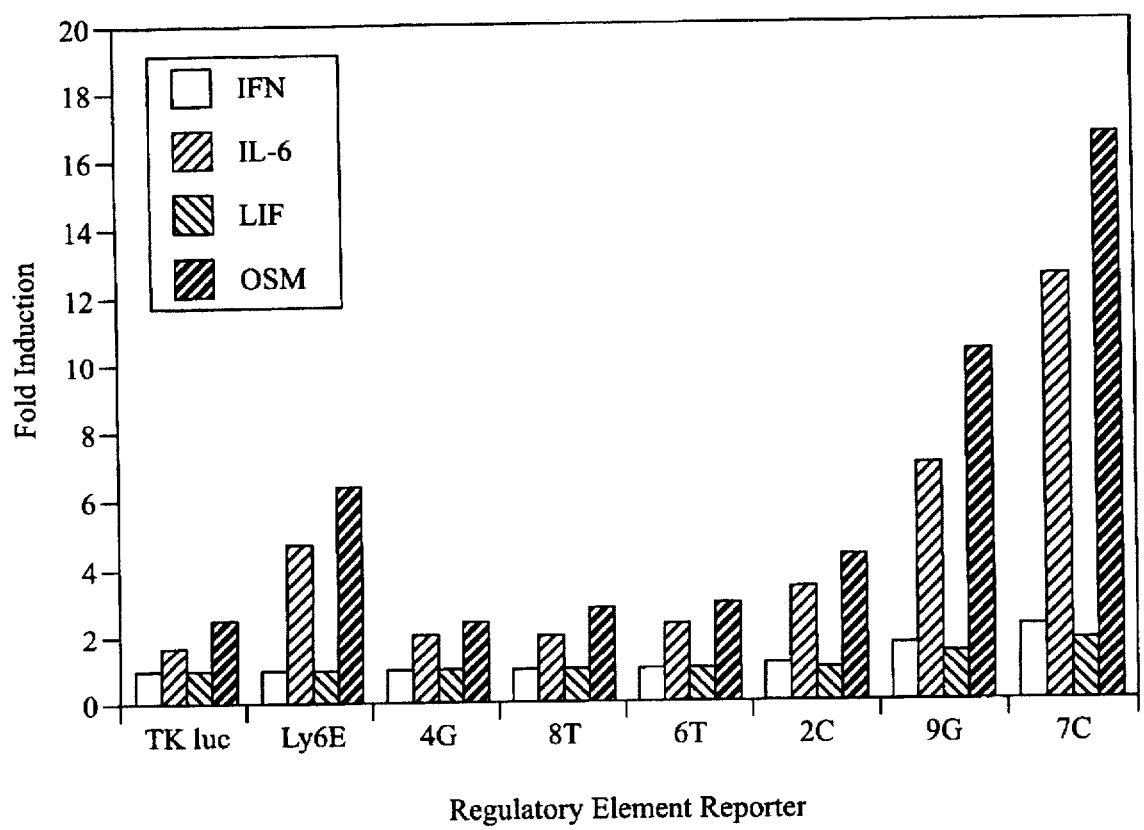
FIG. 3 is a graph showing transcriptional induction mediated by a single Ly6E GAS element and selected regulatory element-containing oligonucleotide sequences of the present invention in response to cytokines. Cells were transfected with reporter plasmids containing a single copy of the inventive regulatory elements or the wild type Ly6E GAS element driving expression of luciferase. Cells were treated with either IFN-γ, IL-6, LIF or OSM as indicated, and induction of transcription over untreated cells determined as described in the Examples. The TK luc control reporter lacks a regulatory element.

Reporter plasmids, constructed as described above, and containing a single copy of the Ly6E GAS element or the 4G (SEQ ID NOs. 29,30), 8T (SEQ ID NOs. 53,54), 6T (SEQ ID NOs. 41,42), 2C (SEQ ID NOs. 19,20), 9G (SEQ ID NOs. 59,60) and 7C (SEQ ID NOs. 49,50) regulatory element-containing oligonucleotide sequences of the present invention were introduced into HepG2 cells and tested for their ability to induce luciferase activity in response to either IFN-γ, IL-6, LIF or OSM. A control plasmid, TK luc, that lacks a regulatory element, was also tested. The results are shown in FIG. 3.

In all cases, IFN-γ or LIF treatment of transfected cells gave no induction of luciferase activity. Surprisingly, both IL-6 and OSM treatment resulted in induction of luciferase activity over background for several of the reporter constructs. The degree of induction by IL-6 or OSM correlated with the ability of the regulatory elements of the selected oligonucleotides to bind to STAT proteins. The construct containing the 7C oligonucleotide, which binds to STATs1α and 3 well, gave the largest inductions, whereas constructs containing regulatory elements that bind STATs less well, such as oligonucleotides 2C and 6T, gave lower inductions. We conclude from these experiments that IL-6 and OSM, but not IFN-γ or LIF, can efficiently activate transcription from a single regulatory element of the present invention in these cells. Thus reporter plasmids containing single regulatory elements according to the present invention exhibit surprising selectivity in their cytokine responsiveness.

Figure 4:
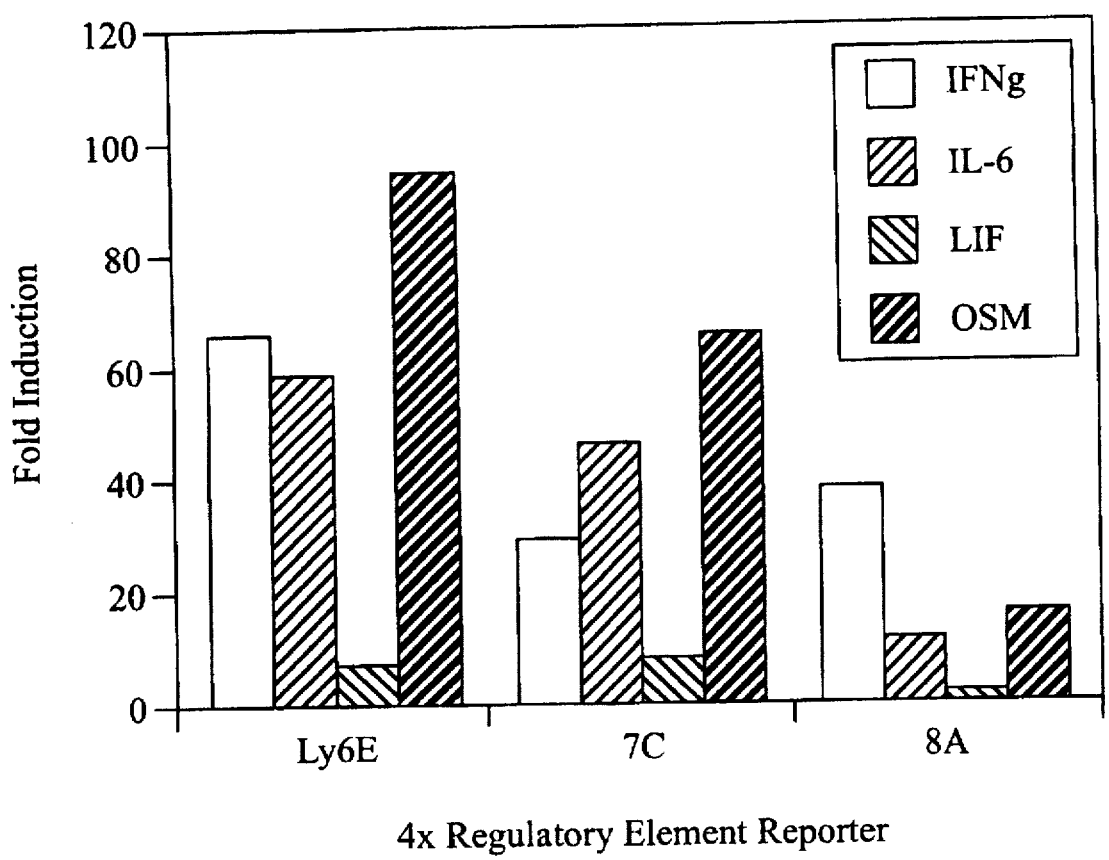
FIG. 4 is a graph showing transcriptional induction mediated by multiple regulatory elements in response to cytokines. Cells were transfected with reporter plasmids containing four copies of either the Ly6E GAS element or the 7C or 8A oligonucleotides containing regulatory elements of the present invention, treated with the indicated cytokines, and fold inductions calculated as described in the Examples.

We next tested the effect of multimerizing selected regulatory elements. Reporter constructs containing 4 copies of the regulatory elements 4G, 7C, 8T and 8A, as well as 4 copies of the Ly6E GAS element were assayed for responsiveness to four test cytokines (FIG. 4). All constructs except 4×4G and 4×8T were responsive to IL-6 and OSM, and gave much larger inductions than the constructs with the corresponding single elements. The degree of induction was not always related to the ability of the elements to bind to STATs in vitro, however. Thus the 4×7C reporter gives lower inductions than the wild type 4×Ly6E reporter, despite binding STAT1α and 3 better in vitro. This is the result of increases in the level of transcription in the absence of cytokine that are larger than the increases in the presence of cytokine, which results in a lowered fold induction. In contrast to the results with single elements, the 4×Ly6E, 4×7C and 4×8A constructs also gave sizable inductions in response to IFN-γ. We also observed differences between the 4×8A construct and the other constructs with respect to the ratio of IFN-γ to IL-6 or OSM induction. The 4×8A construct gave reproducibly larger inductions in response to IFN-γ than to IL-6 or OSM, in contrast to the other constructs tested. This probably reflects the preferential binding of the 8 A mutant to STAT1α versus STAT3 containing complexes, and demonstrates the importance of the precise sequence of the regulatory element in determining response to cytokines.

The constructs containing 4 copies of the 4G and 8T regulatory element-containing oligonucleotide sequences did not give responses to any cytokine tested. Both of these oligonucleotides contain regulatory elements that bind preferentially to STAT1α in the in vitro binding assay, although they do so less avidly than the wild type Ly6E GAS element, or the 7C or 8A regulatory-element containing oligonucleotide sequences, scoring at a level of 3 as opposed to 4 or 5 (FIG. 1). Taken together with the results with the 4×7C, 4×8A and 4×Ly6E constructs, these data lead to the prediction that only regulatory elements having an in vitro binding affinity of 4 or more for STAT1α, on our scale, will mediate transcriptional induction in response to cytokines that activate STAT1α such as IFN-γ (FIG. 5).

Figure 6:
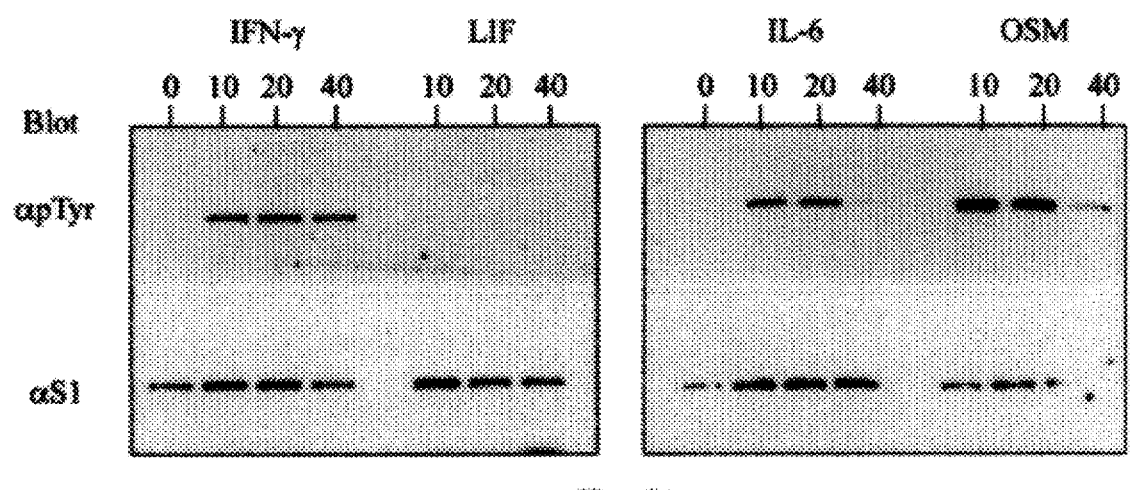
FIG. 6 is a series of gel panels showing tyrosine phosphorylation of STAT1α and STAT3 in response to cytokines. Cells were treated with either IFN-γ, LIF, IL-6 or OSM for the indicated time, and lysates prepared. Lysates were immunoprecipitated with either a STAT1 antisera (top panels) or a STAT3 antisera (bottom panels). After resolution on SDS-polyacrylamide gels and blotting, proteins were detected with antisera directed against either phosphotyrosine, STAT1 or STAT3 as indicated at the left of FIG. 6.
Figure 6:
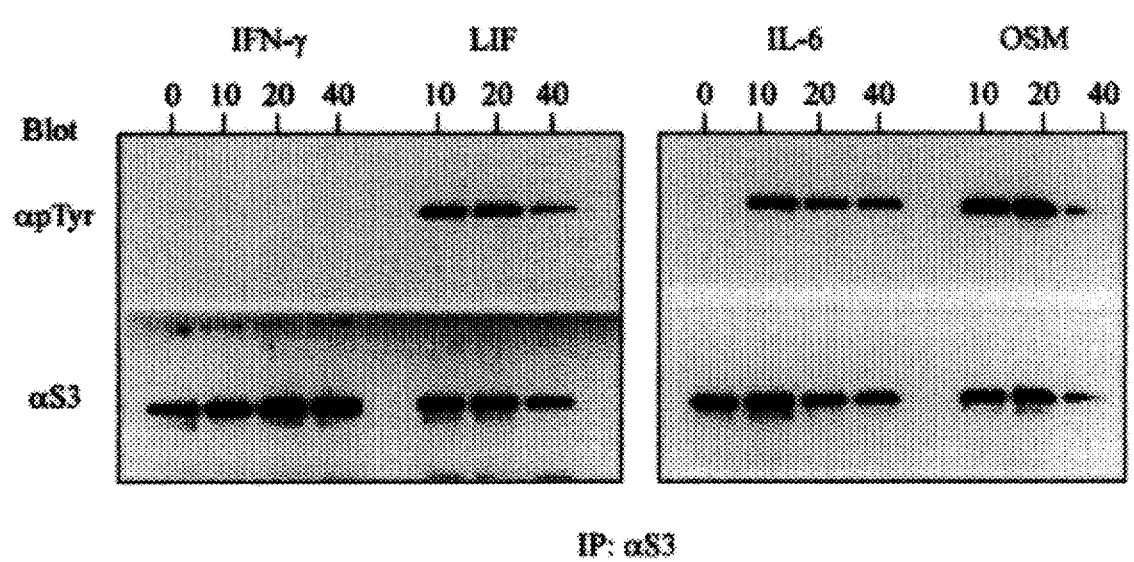

The differential ability of IFN-γ, IL-6, OSM and LIF to activate transcription from regulatory element-containing promoters prompted us to characterize the STATs induced by these cytokines in HepG2 cells. Cells were treated with either IFN-γ, IL-6, OSM or LIF, and lysates were immunoprecipitated with either anti-STAT1 or anti-STAT3 sera (available from Upstate Biotechnology, Inc., N.Y.). The immunoprecipitates were fractionated on SDS-polyacrylamide gels, blotted and proteins detected using a phosphotyrosine antibody. As controls, aliquots of the same immunoprecipitations were blotted and detected with either anti-STAT1 or anti-STAT3 sera. The results are shown in FIG. 6.

IFN-γ, induces rapid tyrosine phosphorylation of STAT1α but no detectable phosphorylation of STAT3. In contrast, LIF induces tyrosine phosphorylation primarily of STAT3, with very low amounts of STAT1α becoming phosphorylated. IL-6 and OSM induce tyrosine phosphorylation of both STAT1α and STAT3, OSM inducing slightly more phosphorylation of both STATs than IL-6. These patterns of STAT activation have been confirmed by gel retardation and antibody supershift experiments (data not shown). Consistent with previous data (Sadowski et al. (1993); Raz et at. (1994) and Zhong et at. (1994)), we interpret these results to indicated that IFN-γ activates a homodimer of STAT1α, LIF induces primarily a homodimer of STAT3 and IL-6 and OSM induce homodimers of STAT1α and STAT3 as well as heterodimers of STAT1α and STAT3. The differences in the ability of IFN-γ, IL-6, OSM and LIF to activate transcription from regulatory element containing reporters is therefore accompanied by differences in their ability to activate STAT1α, STAT3, or both.

These data document the novel finding that reporter plasmids containing single regulatory elements, such as oligonucleotides 7C, 9G and 2C, are responsive to cytokines that activate two STATs, in this case STAT1α and STAT3, such that they form heterodimers. The heterodimer is able to activate transcription from single regulatory elements, whereas homodimers of STAT1α or STAT3 are not. Reporters containing single regulatory elements, including the elements of the present invention, are therefore useful for selectively detecting agonists that mimic the ability of cytokines such as IL-6 to activate both STAT1α and STAT3, allowing heterodimer formation. In addition, the DNA constructs are also useful for detecting antagonists of these cytokines.

The data also document the novel finding that DNA reporter constructs according to the present invention containing multimers of regulatory elements, such as 7C and 8A, are responsive to cytokines that activate STAT1α homodimers or STAT1α/STAT3 heterodimers, but not STAT3 homodimers. These DNA reporter constructs are therefore useful for selectively detecting agonists that mimic the ability of cytokines, such as IFNγ or IL-6, to activate STAT1α homodimers or STAT1α/STAT3 heterodimers. In addition, the DNA constructs are also useful for detecting antagonists of these cytokines.

While in accordance with the patent statutes, description of the preferred weight fractions, and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

---

---

What is claimed is:

1. An isolated DNA molecule 13 to 200 nucleotides in length comprising at least one regulatory element that binds to an activated transcriptional regulatory protein, said regulatory element comprising a nucleotide sequence of TAT-TCCTGGAAGT (SEQ ID No. 1), TATTCCGGTAAGT (SEQ ID No. 2), TCTTCCTGTAAGT (SEQ ID No. 3), TATTCCCGTAAGT (SEQ ID NO. 6), or TATTC-CTATAAGT (SEQ ID No. 7).

2. The isolated DNA molecule according to claim 1, wherein the transcriptional regulatory protein comprises a STAT protein.

3. The isolated DNA molecule according to claim 2, wherein the STAT protein is selected from the group consisting of STAT1α protein, STAT1β protein, STAT2 protein, STAT3 protein, STAT4 protein, STAT5 protein and STAT6.

4. The isolated DNA molecule according to claim 1, wherein the regulatory element binds to an activated transcriptional regulatory protein comprising STAT1α protein in response to a cytokine that activates the STAT1α protein.

5. The isolated DNA molecule according to claim 1, wherein the regulatory element binds to an activated transcriptional regulatory protein comprising STAT1α protein or STAT3 protein in response to a cytokine that activates the STAT1α protein or the STAT3 protein.

6. The isolated DNA molecule according to claim 5, said regulatory element comprising a nucleotide sequence of TATTCCCGTAAGT (SEQ ID No. 6), or TATTC-CTATAAGT (SEQ ID No. 7).

7. The isolated DNA molecule according to claim 1, wherein the regulatory element binds to activated transcriptional regulatory proteins comprising STAT1α protein, STAT3 protein, STAT5 protein or STAT6 protein in response to a cytokine that activates the STAT1α protein, STAT3 protein, STAT5 protein or STAT6 protein.

8. The isolated DNA molecule according to claim 7, said regulatory element comprising a nucleotide sequence of TATTCCTGGAAGT (SEQ ID No. 1), TATTCCGGTAAGT (SEQ ID No. 2), or TCTTCCTGTAAGT (SEQ ID No. 3).

9. The isolated DNA molecule according to claim 1, wherein activation of said activated transcriptional regulatory protein is in response to a cytokine selected from the group consisting of IFNγ, IL-2, IL-3, IL-4, IL-5, IL-6, IL-7, IL-9, IL-10, IL-11, IL-12, IL-13, IL-14, IL-15 GM-CSF, Oncostatin M, growth hormone, G-CSF, Epo, Tpo, EGF, PDGF, CNTF and LIF.

10. The isolated DNA molecule according to claim 1 which is double stranded.

11. A DNA construct comprising a heterologous gene that comprises at least one regulatory element and a promoter operably linked to a structural gene, wherein said structural gene is under the transcriptional control of the regulatory element and promoter, said regulatory element comprising a nucleotide sequence of TATTCCTGGAAGT (SEQ ID No. 1), TATTCCGGTAAGT (SEQ ID No. 2), TCTTCCTGTAAGT (SEQ ID No. 3), TATTCCCGTAAGT (SEQ ID NO. 6), or TATTCCTATAAGT (SEQ IDS No. 7).

12. The DNA construct according to claim 11, wherein the promoter is selected from the group consisting of the gene promoter of the Herpes simplex virus thymidine kinase, adneovirus E1b and yeast alcohol dehydogenase.

13. The DNA construct according to claim 11, wherein the heterologous gene comprises a structural gene for luciferase, chloramphenicol acetyl transferase, β-galactosidase, secreted placental alkaline phosphatase, human growth hormone, t-PA, green fluorescent protein or inteferon.

14. The DNA construct according to claim 11, wherein the heterologous gene comprises a multimer of at least one of the regulatory elements.

15. The DNA construct according to claim 11, wherein the heterologous gene comprises the gene promoter of the Herpes simplex virus thymidine kinase and a structural gene for luciferase.

16. A host cell transfected with the DNA construct of claim 11.

17. A method for the controlled expression of a heterologous gene of interest comprising culturing the cells of claim 16 in the presence of a cytokine.

18. A method for detecting the presence of a transcriptional regulatory protein in a sample comprising contacting the sample with the isolated DNA molecule according to claim 1 under conditions where the transcriptional regulatory protein is activated and binds with the isolated DNA molecule to form a complex, and detecting the presence of the complex in the sample.

19. The method according to claim 18, further comprising, separating the complex from the sample and the isolated DNA molecule from the complex to yield the transcriptional regulatory protein.

20. A method for measuring the ability of a compound to act as an agonist of gene transcription comprising:

(a) contacting the compound with the host cell according to claim 16 under conditions in which the heterologous gene is expressed in response to the compound; and (b) comparing the level of gene expression in step (a) with the level of gene expression from the host cell in the absence of the compound, wherein the ability of the compound to act as an agonist of gene transcription is measured as the increase in the level of gene expression in step (a) compared to the level of gene expression from the host cell in the absence of the compound.

21. The method according to claim 20, wherein the heterologous gene comprises a structural gene for luciferase, chloramphenicol acetyl transferase, β-galactosidase, green fluorescent protein or secreted placental alkaline phosphatase.

22. A method for measuring the ability of a compound to act as an antagonist of gene transcription comprising:

(a) contacting the compound with the host cell according to claim 16 in the presence of a predetermined amount of a signaling molecule under conditions in which the heterologous gene is expressed in response to the signaling molecule; and (b) comparing the level of gene expression in step (a) with the level of gene expression from the host cell in the presence of the cytokine, but the absence of the compound, wherein the ability of the compound to act as an antagonist of gene transcription is measured as the amount of decrease in the level of gene expression in step (a) compared to the level of gene expression from the host cell in the presence of the cytokine and absence of the compound.

23. The method according to claim 22, wherein the heterologous gene comprises a structural gene for luciferase, chloramphenicol acetyl transferase, β-galactosidase, green fluorescent protein or secreted placental alkaline phosphatase.

24. An isolated DNA molecule 13 to 200 nucleotides in length comprising at least one regulatory element, said regulatory element comprising a nucleotide sequence of TATTCCTGGAAGT (SEQ ID No. 1), TATTCCGGTAAGT (SEQ ID No. 2), TCTTCCTGTAAGT (SEQ ID No. 3), TATTCCCGTAAGT (SEQ ID NO. 6), or TATTCTATAAGT (SEQ ID No. 7), or a complement thereof.

25. The isolated DNA molecule according to claim 24, wherein the isolated DNA molecule comprises a multimer of at least one of the regulatory elements.

26. A method for measuring the ability of a compound to agonize or antagonize the induction of STAT heterodimers comprising:

(a) contacting the compound with the host cell according to claim 16 under conditions in which the heterologous gene is expressed in response to the compound, wherein the host cell is transfected with a DNA construct comprising a single copy of said regulatory element that selectively binds to an activated STAT heterodimer; and (b) comparing the level of gene expression in step (a) with the level of gene expression from the host cell in the absence of the compound, wherein the ability of the compound to act as an antagonist of the induction of STAT heterodimers is measured as the amount of decrease in the level of gene expression in step (a) compared to the level of gene expression from the host cell in the absence of the compound and wherein the ability of the compound to act as an agonist of the induction of STAT heterodimers is measured as the amount of increase in the level of gene expression in step (a) compared to the level of gene expression from the host cell in the absence of the compound.

27. The method according to claim 26, wherein the STAT heterodimer comprises a STAT1α/STAT3 heterodimer.

\* \* \* \* \*